(12) United States Patent
Lauber et al.

(10) Patent No.: US 7,663,024 B2
(45) Date of Patent: Feb. 16, 2010

(54) P15 HAIRPIN CONSTRUCTS AND USE

(75) Inventors: Emmanuelle Lauber, Castanet-Tolosan (FR); Hubert Guilley, Berstett (FR); Ken Richards, Pfulgriesheim (FR); Gerard Jonard, Berstett (FR); Elodie Klein, Strasbourg-Neudorf (FR); David Gilmer, Strasbourg (FR)

(73) Assignee: Sesvanderhave, N.V., Tienen (BE)

( * ) Notice: Subject to any disclaimer, the term of this patent is extended or adjusted under 35 U.S.C. 154(b) by 295 days.

(21) Appl. No.: 11/418,384

(22) Filed: May 3, 2006

(65) Prior Publication Data

US 2006/0288445 A1 Dec. 21, 2006

(51) Int. Cl.
- *A01H 1/00* (2006.01)
- *C12N 15/82* (2006.01)
- *C12N 15/87* (2006.01)
- *C07H 21/04* (2006.01)

(52) U.S. Cl. ............... 800/285; 800/279; 536/23.72

(58) Field of Classification Search ............ None
See application file for complete search history.

(56) References Cited

U.S. PATENT DOCUMENTS

| | | | | |
|---|---|---|---|---|
| 6,297,428 | B1 * | 10/2001 | Guilley et al. | 800/280 |
| 6,835,538 | B1 * | 12/2004 | Lauber et al. | 435/6 |
| 2002/0169298 | A1 | 11/2002 | Waterhouse et al. | |

FOREIGN PATENT DOCUMENTS

| | | | |
|---|---|---|---|
| WO | WO 91/13159 | | 9/1991 |
| WO | WO 98/07875 | | 2/1998 |
| WO | WO98/07875 | * | 2/1998 |
| WO | WO 00/03025 A | | 1/2000 |

OTHER PUBLICATIONS

Thomas et al. 2001, The Plant Journal 25(4):417-425.*
Sequence alignment of SEQ ID No. 3 against SEQ ID No. 1 of US 6,297,428.*
Fagoaga C. et al. (2006) "Post-transcriptional gene silencing of the p23 silencing suppressor of *Citrus tristeza virus* confers resistance to the virus in transgenic Mexican lime" *Plant Molec. Biol.* 60:153-165.
Foster T.M. et al. (2002) "A surveillance system regulates selective entry of RNA into the shoot apex" *Plant Cell* 14:1497-1508.
Haupt S. et al. (2005) "Two plant-viral movement proteins traffic in the endocytic recycling pathway" *Plant Cell* 17:164-181.
International Search Report from PCT/EP2007/054259, dated Jan. 10, 2008.
Koenig R. et al. (1998) "Genome properties of beet virus Q, a new furo-like virus from sugarbeet, determined from unpurified virus" J. Gen. Virol. 79:2027-2036.
Missiou A. et al. (2004) "Generation of transgenic potato plants hightly resistant to potato virus Y (PVY) through RNA silencing" *Molecular Breeding* 14:185-197.
Bouzoubaa, et al. 1986, Nucleotide sequence of beet necrotic yellow vein virus RNA-2. J. Gen. Virol., 67:1689-1700.
Gilmer, et al., Efficient Cell-to-Cell Movement of Beet Necrotic Yellow Vein Virus Requires 3' Proximal Genes Located on RNA 2, Virology 189, pp. 40-47.
Xu, et al. Genetically engineered resistance to potato virus X in four commercial potato cultivars. Plant Cell Reports, Vo. 15 1995. pp. 91-96.
Seppanen, et al. Movement protein-derived resistance to triple gene block-containing plant viruses. Journal of General Virology, vol. 78, 1997, pp. 1241-1246.
Beck, et al. Disruption of virus movement confers broad-spectrum resistance against systemic infection by plant viruses with a triple gene blockPlant Biology Acad Sci USA, vol. 91, Oct. 1994, pp. 10310-10314.
PCT International Search Report for PCT BE99 00089.
Higgins, N. et al. (2001) "Chromosome Structure" *Encyclopedia of Life Sciences*, Macmillan Publishers Ltd. Nature Publishing Group, pp. 1-10.
Raska, I. et al. (2004) "The nucleolus and transcription of ribosomal genes" *Biology of the Cell* 96:579-594.
Tamada, T. et al. (1996). "Evidence that beet necrotic yellow vein virus RNA-5 is involved in symptom development of sugar-beet roots" In *Proceedings of the Third Symposium of the International Working Group on Plant Viruses with Fungal Vectors*, pp. 49-52. Edited by J. L. Sherwood & C. M. Rush. Denver: American Society of Sugar Beet Technologists.
Zuker, M. et al. (1981) "Optimal computer folding of large RNA sequences using thermodynamics and auxiliary information" *Nucleic Acids Research* 9:133-148.

* cited by examiner

*Primary Examiner*—Ashwin Mehta
*Assistant Examiner*—Li Zheng
(74) *Attorney, Agent, or Firm*—Knobbe Martens Olson & Bear LLP

(57) ABSTRACT

The present invention concerns a method of genetic modification of a TGB-3 wild type viral sequence for reducing or suppressing the possible deleterious effects of the agronomic properties of a transformed plant or plant cell by said TGB-3 viral sequence. The invention further relates to genetically modified TGB-3 viral sequences suitable to induce gene silencing. In particular hairpin constructs based on such sequences proved highly efficient to induce a PTGS mechanism and degradation of the whole of RNA2 thereby. When plants are transformed accordingly the spread of the virus in the plant is significantly reduced or blocked.

58 Claims, 7 Drawing Sheets

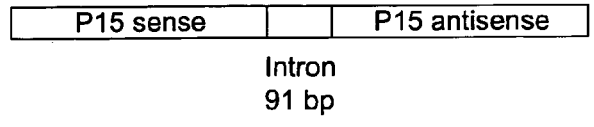

FIG. 1A

```
ATCGTGCTTG TGGTTAAAGT AGATTTATCT AATATTGTAT TGTACATAGT
TGCCGGTTGT GTTGTTGTCA GTATGTTGTA CTCACCGTTT TTCAGCAACG
ATGTTAAAGC GTCCAGCTAT GCGGGAGCAA TTTTTAAAGG GAGCGGCTGT
ATCATGGCCG CGAATTCGTT TGCTCAATTT GGGAGTTGCG ATATTCCAAA
GCATGTAGCC GAGTCCATCA CTAAGGTTGC CACCAAAGAG CACGATGTTG
ACATAATGGT AAAAAGGGGT GAAGTGACCG TTCGTGTTGT GACTCTCACC
GAAACTATTT TTATAATATT ATCTAGATTG TTTGGTTTGG CGGTGTTTTT
GTTCATGATA TGTTTAATGT CTATAGTTTG GTTTTGGTAT CATAGACAAG
GTACCTAAAT CCTGGTTTTA TATGTACTAC TGTTGTAGCT GAAATTTAGG
TCTTCTTGCT GAAATTTATT TCTGTTTCGT TTTCACTGTT ATTCAGTATC
GATTTGTCTA TGATACCAAA ACCAAACTAT AGACATTAAA CATATCATGA
ACAAAAACAC CGCCAAACCA ACAATCTAG ATAATATTAT AAAAATAGTT
TCGGTGAGAG TCACAACACG AACGGTCACT TCACCCCTTT TTACCATTAT
GTCAACATCG TGCTCTTTGG TGGCAACCTT AGTGATGGAC TCGGCTACAT
GCTTTGGAAT ATCGCAACTC CCAAATTGAG CAAACGAATT CGCGGCCATG
ATACAGCCGC TCCCTTTAAA AATTGCTCCC GCATAGCTGG ACGCTTTAAC
ATCGTTGCTG AAAAACGGTG AGTACAACAT ACTGACAACA ACACAACCGG
CAACTATGTA CAATACAATA TTAGATAAAT CTACTTTAAC CAC AAGCACG
AT                  (SEQ ID NOS 9, 10, 11and 12)
```

FIG. 1B

| P15 sense | Intron 550bp | P15 antisense |

*FIG. 2A*

ATCGTGCTTG TGGTTAAAGT AGATTTATCT AATATTGTAT TGTACATAGT
TGCCGGTTGT GTTGTTGTCA GTATGTTGTA CTCACCGTTT TTCAGCAACG
ATGTTAAAGC GTCCAGCTAT GCGGGAGCAA TTTTTAAAGG GAGCGGCTGT
ATCATGGCCG CGAATTCGTT TGCTCAATTT GGGAGTTGCG ATATTCCAAA
GCATGTAGCC GAGTCCATCA CTAAGGTTGC CACCAAAGAG CACGATGTTG
ACATAATGGT AAAAAGGGGT GAAGTGACCG TTCGTGTTGT GACTCTCACC
GAAACTATTT TTATAATATT ATCTAGATTG TTTGGTTTGG CGGTGTTTTT
GTTCATGATA TGTTAATGT CTATAGTTTG GTTTGGTAT CATAGACAAG
*GTACC*ACGTT TTTCTCTCTC CTAATTTTTC TCACTTTTTT TTCATCTCAT
TCTGTTTTAT GTTCTGTGAA TTTATTAGTA GATTATCTA CTTTTCTATC
TAATTTTGAC GCTAGATTAA TGATTCAGTT TTATTATTAC ATTTTCCGGA
AAATTGGTTA AGTTTTGATA ATTTAAATGA TTTTTTTCC GTGATCAAAT
TGTAGAAATT GTTTAAGTTC GATAGTTTAT ATCTTTATGA ATTTTTGTGT
TTGATCTGAT GATAGTTTTA GTGATTATTG TAACTTTTGA AAGTGTGTGT
TTTTATGTGT GTAGCGATTT GTATAGTAAA TAAGATTAAT GATCATGGCT
AAATTATGGC GTAGGTTAAT TTTAGAAGAA AGTATTTTTT TGCTAAATTG
AAGTCATCTG CGTCGTATTA TTGCGATTTC TGCACTTTTA CTAGCTGAAT
TGAGTTTGCT GATTGGATAT TCTTTATGAT TGAAGTTGTT TTGCTATTGA
ATATTCTTTA TGAGATTTTT GAATGAAGAT TTTTCTGTAA TTAATATGAT
CAGGT*ATCGA* TTTGTCTATG ATACCAAAAC CAAACTATAG ACATTAAACA
TATCATGAAC AAAAACACCG CCAAACCAAA CAATCTAGAT AATATTATAA
AAATAGTTTC GGTGAGAGTC ACAACACGAA CGGTCACTTC ACCCCTTTTT
ACCATTATGT CAACATCGTG CTCTTTGGTG GCAACCTTAG TGATGGACTC
GGCTACATGC TTTGGAATAT CGCAACTCCC AAATTGAGCA AACGAATTCG
CGGCCATGAT ACAGCCGCTC CCTTTAAAAA TTGCTCCCGC ATAGCTGGAC
GCTTTAACAT CGTTGCTGAA AAACGGTGAG TACAACATAC TGACAACAAC
ACAACCGGCA ACTATGTACA ATACAATATT AGATAAATCT ACTTTAACCA
CAAGCACGAT            (SEQ ID NOS 13, 9, 14nd 12)

*FIG. 2B*

```
ATGGTGCTGCTTGTGGTTAAAGTAGATTTATCTAATATTGTATTGTATGTACATAGTTGCCGGTTGT  60
 M  V  L  V  V  K  V  D  L  S  N  I  V  L  Y  I  V  A  G  C
GTTGTTGTCAGTATGTTGTACTCACCGTTTTCAGCAACGATGTTAAAGCGTTCCAGCTAT 120
 V  V  V  S  M  L  Y  S  P  F  F  S  N  D  V  K  A  S  S  Y
GCGGGAGCAATTTTTAAGGGGAGCGGCTGTATCATGGACAGGAATTCGTTTGCTCAATTT 180
 A  G  A  I  F  K  G  S  G  C  I  M  D  R  N  S  F  A  Q  F
GGGAGTTGCGATATTCCAAAGCATGTAGCCGAGTCCATCACTAAGGTTGCCAAAGAG 240
 G  S  C  D  I  P  K  H  V  A  E  S  I  T  K  V  A  T  K  E
CACGATGTGACATAATGGTAAAAGGGGTGAAGTACCGTTCGTGTGACTCTCACC 300
 H  D  V  D  I  M  V  K  R  G  E  V  T  V  R  V  V  T  L  T
GAAACTATTTTTATAATATATCTAGATTGTTTGGTTTTGGTGTTTGTTCATGATA 360
 E  T  I  F  I  L  S  R  L  F  G  L  A  V  F  L  F  M  I
TGTTTAAATGTCTATAGTTTGGTTTTGGTATCATAGATAA 399               (SEQ ID NO 7)
 C  L  M  S  I  V  W  F  W  Y  H  R  *                     (SEQ ID NO 8)
```

FIG.3

ATCGTGCTTGTGGTTAAAGTAGATTATCTAATATTGTATTGTACATAGTTGCCGGTTGT 60
GTTGTTGTCAGTATGTTGTACTCACCGTTTTTCAGCAACGATGTTAAAGCGTCCAGCTAT 120
GCGGGAGCAATTTTAAGGGAGGCGGCTGTATCATGGCCGCGAATTCGTTTGCTCAATTT 180
GGGAGTTGCGATATTCCAAAGCATGTAGCCGAGTCCATCACTAAGGTTGCCACCAAAGAG 240
CACGATGTTGACATAATGGTAAAAAGGGGTGAAGTGACCGTTCGTGTTGACTCTCACC 300
GAAACTATTTTATAATATTCTAGATTGTTTGGTTTGGCGGTGTTTTTGTTCATGATA 360
TGTTAATGTCTATAGTTTGGTTTTGGTATCATAGACAA 399

(SEQ ID NO 10)

FIG.8

P15 HAIRPIN CONSTRUCTS AND USE

CROSS-REFERENCE TO RELATED APPLICATIONS

Field of the Invention

The present invention relates to hairpin DNA constructs and to their use to induce post-transcriptional gene silencing (PTGS) in plants, and more in particular sugar beet plants, with the aim of obtaining plants that exhibit an increased resistance or tolerance to a virus such as beet necrotic yellow vein virus (BNYVV). The present invention further relates to transgenic cells and plants that exhibit an increased resistance to e.g. BNYVV and to their progeny.

BACKGROUND OF THE INVENTION

An area of deep interest is the conferral upon plants of resistance or tolerance to viruses. In crops, large proportions of the harvest may be lost due to virus infections.

The widespread viral disease of the sugar beet plant (*Beta vulgaris*) called Rhizomania is caused by a furovirus, the beet necrotic yellow vein virus (BNYVV) (1, 2) which is transmitted to the root of the beet by the soilborne fungus *Polymyxa betae* (3).

The disease affects significantly acreages of the area where the sugar beet plant is grown for industrial use in Europe, USA and Japan and is still in extension in several places in Western Europe (4, 5).

Since 1986, a number of reports and publications have described the use of isolated viral nucleotidic sequences expressed in plants to confer a high level of tolerance against a specific infectious virus or even to confer a broad spectrum type of resistance against a number of related viruses (6, 7, 8). One of the most documented viral resistance strategy based on genetic engineering, in many cultivated species such as potato, squash, cucumber or tomato, is the use of the viral nucleotidic sequence which under the control of plant regulatory elements, encodes the coat-protein of the target virus (9).

However, even in coat-protein mediated resistance, the expression of a certain level of resistance in the transgenic plant might be attributed to different mechanisms such as RNA co-suppression or a protein mediated resistance triggered by the production of a protein sequence.

In general, the viral sequence will be transformed in an appropriate cell or tissue culture of the plant species using an *Agrobacterium* mediated transformation system or a direct gene transfer method according to the constraints of the tissue culture or cell culture method which can be successfully applied in a given species. A whole plant will be regenerated and the expression of the transgene will be characterized.

Though sugar beet has been known as a recalcitrant species in cell culture, limiting the extent of practical genetic engineering applications in that species, there is now a growing number of reports of successful transformation and regeneration of whole plants (38). A few examples of engineering tolerance to the BNYVV by transforming and expressing the BNYVV coat-protein sequence in the sugar beet genome have also been published (11, WO91/13159) though they rarely report data on whole functional transgenic sugar beet plants (12). In particular, reports show limited data on the level of actual resistance observed in infected conditions with transgenic sugar beet plants transformed with a gene encoding a BNYVV coat-protein sequence (13, 14).

A complete technology package including a sugar beet transformation method and the use of the expression of the BNYVV coat-protein sequence as resistance source in the transgenic sugar beet plant obtained by said transformation method has been described in the Patent Application WO91/13159.

Based on the information published, it can not be concluded that the coat-protein mediated resistance mechanism provides any potential for conferring to the sugar beet plant a total immunity to the BNYVV-infection by inhibiting completely the virus multiplication and diffusion mechanisms. To identify a resistance mechanism which significantly blocks the spread of the virus at the early stage of the infection process would be a major criterium of success to develop such a transgenic resistance. In addition, such resistance would diversify the mechanisms of resistance available.

Because the disease is shown to expand in many countries or areas, at a speed depending upon the combination of numerous local environmental and agricultural factors, there is a major interest to diversification and improvement of the genetic resistance mechanisms which may, alone or in combination, confer a stable and long lasting resistance strategy in the current and future varieties of sugar beet plants which are grown for industrial use.

The genome of beet necrotic yellow vein furovirus (BNYVV) consists of five plus-sense RNAs, two of which (RNAs 1 and 2) encode functions essential for infection of all plants while the other three (RNAs 3, 4 and 5) are implicated in vector-mediated infection of sugar beet (*Beta vulgaris*) roots. Cell-to-cell movement of BNYVV is governed by a set of three successive, slightly overlapping viral genes on RNA 2 known as the triple gene block (TGB), which encode, in order, the viral proteins P42, P13 and P15 (gene products are designated by their calculated Mr in kilodalton).

In the following description, the TGB genes and the corresponding proteins will be identified by the following terms: TGB-1, TGB-2, TGB-3 or by their encoded viral protein number P42, P13 and P15. TGB counterparts are present in other furoviruses and in potex-, carla- and hordeiviruses (15, 18, 19, 20, 21 and 22). The enclosed table 1 represents viruses having a TGB-3 sequence, the molecular weight of TGB-3 of said viruses, their host and references.

It has been shown previously that independent expression of P15 from a viral-RNA replication species known as a "replicon", derived from BNYVV RNA 3, inhibits infection with BNYVV by interfering cell-to-cell movement (16).

In order to introduce a virus comprising a TGB-3 nucleic acid sequence into a plant cell or a plant, it has been proposed to incorporate a nucleic acid construct comprising said TGB-3 nucleic acid sequence operably linked to one or more regulatory sequences active in said plant (WO98/07875).

However, while expression of wild type TGB-3 viral sequence in a transgenic plant allows the blocking of said viral infection, the presence of said wild type sequence may induce deleterious effects on the agronomic properties of transformed plants or plant cells. The present invention resides in the finding that some mutated (genetically modified) TGB-3 viral sequences disclosed in the present invention are highly useful in the genetic engineering of BNYVV resistant (sugar) beet plants.

Aims of the Invention

The present invention aims to provide more reliable methods and means to confer viral resistance, e.g. BNYVV viral resistance, advantageously extreme BNYVV resistance, upon plants, more in particular upon sugar beet plants by genetically modifying or transforming plant cells.

The present invention further aims to provide genetically modified or transformed plant cells obtainable as such, which may be regenerated into plants that exhibit increased tolerance or resistance to the plant virus e.g. BNYVV.

Yet another aim is to provide resistant progeny, e.g. BNYVV resistant progeny, seeds and other reproducible organs or structures originating from such transformed plants and plant cells.

SUMMARY OF THE INVENTION

It seems that the function of the TGB-3 wild type sequence in cell-to-cell movement involves at least in part "bridging" interactions between an element of the host plant (preferably a component of the plasmodesmata), and an element of viral origin (preferably another viral protein involved in cell-to-cell movement). Disruption of either the domain of the TGB-3 wild type sequence (which putatively interacts with the host element) or the domain of the TGB-3 wild type sequence (which putatively interacts with the viral element), allows the inhibition of the cell-to-cell movement.

In addition, it seems that said specific mutations in a TGB-3 wild type sequence allow the production of mutants produced in a transgenic plant, which will still interact with the viral element, but not with the host element. These mutants might compete for binding sites on the viral element of the TGB-3 wild type sequence produced in the initial stage of the viral infection, and abort the infection by inhibiting viral movement to an adjacent cell.

Advantageously, the substitution of at least one amino-acid into another different amino-acid of said sequence is made in regions rich in hydrophilic amino-acids usually present at the surface of the protein in its native configuration.

Preferably, the point mutation(s) allow the substitution of one or two amino-acids into one or two different amino-acids.

In the enclosed Table 1, preferred examples of said viruses having a TGB-3 wild type viral sequence, the molecular weight of the corresponding TGB-3 peptide, their hosts and a reference, are described. The specific wild type P15 nucleotidic and amino-acid sequences of BNYVV are also already described (17, the wild-type sequences enclosed by reference herein).

The above-described point mutations were realized by conventional methods known by the person skilled in the art.

The above mutants containing the point mutation were tested for their ability to promote cell-to-cell movement of a viral mutant (with a dysfunctional TGB-3 sequence, preferably a BNYVV mutant with a dysfunctional P15 gene) when expressed in trans from a replicon. These mutants were incapable of promoting such movement and were tested for their ability to inhibit infection with a co-inoculated wild type TGB-3 virus, preferably co-inoculated with a wild type BNYVV, when the mutant form of the TGB-3 sequence, preferably the P15 gene, was expressed from a replicon.

The Inventors have discovered unexpectedly that the genetic modification method according to the invention (preferably a point mutation) could be used to obtain a modified TGB-3 viral sequence (preferably a modified BNYVV P15 sequence), which is able to block virus infection without producing deleterious effects when incorporated in the genome of a plant or a plant cell. A first aspect according to the invention is related thereto.

It is meant by "being able to block viral infection into a plant or a plant cell", the possibility to obtain a high degree of tolerance by the plant or plant cell transformed by said modified TGB-3 viral sequence to said viral infection, in particular the possibility to ensure rapid and total blocking of the virus multiplication and diffusion mechanisms into the plant, preferably the blocking of the BNYVV virus multiplication and diffusion mechanisms into a sugar beet plant (*beta vulgaris*), including fodder beet, Swiss Chard and table beet which may also be subjected to said BNYVV infection.

Said tolerance or resistance could be easily measured by various methods well known by the person skilled in the art.

Preferably, the genetic modifications in the TGB-3 wild type viral sequence are point mutations in the portions of said wild type viral sequence involved in the mechanisms of viral cell-to-cell movements.

The present invention is also related to the modified TGB-3 viral nucleotidic and amino-acid sequences obtained (recovered) by said (modification and selection) method, more preferably the BNYVV P15 modified nucleotidic and amino-acid sequences obtained (recovered) by said method.

Preferably, said BNYVV P15 nucleotidic and amino-acid sequences are selected from the group consisting of the following nucleotidic (SEQ ID NOs: 1, 3 and 5) or corresponding amino-acid sequences (SEQ ID Nos: 2, 4 and 6):

```
SEQ ID NO: 1
ATGGTGCTTGTGGTTGCAGTAGCTTTATCTAATATTGTATTGTACATAGTTGCCGGTTGT    60

SEQ ID NO: 2
M   V   L   V   V   A   V   A   L   S   N   I   V   L   Y   I   V   A   G   C

GTTGTTGTCAGTATGTTGTACTCACCGTTTTTCAGCAACGATGTTAAAGCGTCCAGCTAT    120
V   V   V   S   M   L   Y   S   P   F   F   S   N   D   V   K   A   S   S   Y

GCGGGAGCAATTTTTAAGGGGAGCGGCTGTATCATGGACAGGAATTCGTTTGCTCAATTT    180
A   G   A   I   F   K   G   S   G   C   I   M   D   R   N   S   F   A   Q   F

GGGAGTTGCGATATTCCAAAGCATGTAGCCGAGTCCATCACTAAGGTTGCCACCAAAGAG    240
G   S   C   D   I   P   K   H   V   A   E   S   I   T   K   V   A   T   K   E

CACGATGTTGACATAATGGTAAAAAGGGGTGAAGTGACCGTTCGTGTTGTGACTCTCACC    300
H   D   V   D   I   M   V   K   R   G   E   V   T   V   R   V   V   T   L   T

GAAACTATTTTTATAATATTATCTAGATTGTTTGGTTTGGCGGTGTTTTTGTTCATGATA    360
E   T   I   F   I   I   L   S   R   L   F   G   L   A   V   F   L   F   M   I

TGTTTAATGTCTATAGTTTGGTTTTGGTATCATAGATAA                         399
C   L   M   S   I   V   W   F   W   Y   H   R   *
```

-continued

```
SEQ ID NO: 3
ATGGTGCTTGTGGTTAAAGTAGATTTATCTAATATTGTATTGTACATAGTTGCCGGTTGT      60

SEQ ID NO: 4
 M   V   L   V   V   K   V   D   L   S   N   I   V   L   Y   I   V   A   G   C

GTTGTTGTCAGTATGTTGTACTCACCGTTTTTCAGCAACGATGTTAAAGCGTCCAGCTAT     120
 V   V   V   S   M   L   Y   S   P   F   F   S   N   D   V   K   A   S   S   Y

GCGGGAGCAATTTTTAAGGGGAGCGGCTGTATCATGGCCGCGAATTCGTTTGCTCAATTT     180
 A   G   A   I   F   K   G   S   G   C   I   M   A   A   N   S   F   A   Q   F

GGGAGTTGCGATATTCCAAAGCATGTAGCCGAGTCCATCACTAAGGTTGCCACCAAAGAG     240
 G   S   C   D   I   P   K   H   V   A   E   S   I   T   K   V   A   T   K   E

CACGATGTTGACATAATGGTAAAAAGGGGTGAAGTGACCGTTCGTGTTGTGACTCTCACC     300
 H   D   V   D   I   M   V   K   R   G   E   V   T   V   R   V   V   T   L   T

GAAACTATTTTTATAATATTATCTAGATTGTTTGGTTTGGCGGTGTTTTTGTTCATGATA     360
 E   T   I   F   I   I   L   S   R   L   F   G   L   A   V   F   L   F   M   I

TGTTTAATGTCTATAGTTTGGTTTTGGTATCATAGATAA                          399
 C   L   M   S   I   V   W   F   W   Y   H   R   *

SEQ ID NO: 5
ATGGTGCTTGTGGTTAAAGTAGATTTATCTAATATTGTATTGTACATAGTTGCCGGTTGT      60

SEQ ID NO: 6
 M   V   L   V   V   K   V   D   L   S   N   I   V   L   Y   I   V   A   G   C

GTTGTTGTCAGTATGTTGTACTCACCGTTTTTCAGCAACGATGTTAAAGCGTCCAGCTAT     120
 V   V   V   S   M   L   Y   S   P   F   F   S   N   D   V   K   A   S   S   Y

GCGGGAGCAATTTTTAAGGGGAGCGGCTGTATCATGGCCGCGAATTCGTTTGCTCAATTT     180
 A   G   A   I   F   K   G   S   G   C   I   M   A   A   N   S   F   A   Q   F

GGGAGTTGCGATATTCCAAAGCATGTAGCCGAGTCCATCACTAAGGTTGCCACCAAAGAG     240
 G   S   C   D   I   P   K   H   V   A   E   S   I   T   K   V   A   T   K   E

CACGATGTTGACATAATGGTAAAAAGGGGTGAAGTGACCGTTCGTGTTGTGACTCTCACC     300
 H   D   V   D   I   M   V   K   R   G   E   V   T   V   R   V   V   T   L   T

GAAACTATTTTTATAATATTATCTAGATTGTTTGGTTTGGATGATTTTTTGTTCATGATA     360
 E   T   I   F   I   I   L   S   R   L   F   G   L   D   D   F   L   F   M   I

TGTTTAATGTCTATAGTTTGGTTTTGGTATCATAGATAA                          399
 C   L   M   S   I   V   W   F   W   Y   H   R   *
```

In the following description, the various modified BNYVV TGB-3 sequences will be hereafter called "P15 mutants", identified by the following reference: BNP15-Ala1, corresponding to SEQ ID NO 1; BNP15-Ala4 corresponding to SEQ ID NO 3; BNP15-Asp9, corresponding to SEQ ID NO 5.

The nucleotidic and corresponding amino-acid sequences of SEQ ID NO 1, SEQ ID NO 3 and SEQ ID NO 5 can be compared to SEQ ID NO 7, which is the sequence of the wild type P15 nucleotidic and amino-acid sequence (SEQ ID NO 8) already described (17).

The present invention is also related to the vector comprising said modified nucleotidic sequence or a fragment thereof possibly being operably linked to one or more regulatory sequence(s) active into a plant or a plant cell. Preferably, said vector is a plasmid comprising already said regulatory sequence(s) active into a plant or a plant cell. The vector may also be a cassette nucleotide sequence consisting of only a nucleotide sequence of interest to be inserted in the genome of a plant (in this case a modified BNYVV TGB-3 sequence or a fragment thereof), which is associated with one or more promoter(s), terminal nucleotide sequences and possibly regulatory sequences sufficient to obtain an efficient expression of the sequences of interest, yet that is further (substantially) free from other prokaryotic or plasmidic nucleotide sequences (see EP 1 174 513).

The present invention is also related to a method for inducing a resistance to a virus comprising a TGB-3 sequence, preferably one of the viruses described in the enclosed Table 1, and more preferably the BNYVV virus, said method comprising the following steps:
 preparing a nucleic acid construct comprising a nucleic acid sequence being genetically modified according to the method according to the invention, or comprising a fragment of such modified sequence, and being operably linked to one or more regulatory sequences active into a plant or a plant cell,
 transforming the plant cell with the nucleic acid construct, and
 possibly regenerating the transgenic plant from the transformed plant cell.

Preferably, said method is used for inducing a resistance to the BNYVV into a sugar beet plant or a sugar beet cell. Said method comprises the following steps:
 preparing a nucleic acid construct comprising a modified nucleic acid sequence obtained by the method according to the invention, or comprising a fragment of such modified sequence, preferably preparing a nucleic acid construct comprising a nucleic acid sequence selected from the group consisting of SEQ ID NO 1, SEQ ID NO 3 or SEQ ID NO 5, or a fragment of any of these, being operably linked to one or more regulatory sequences active into a plant, transforming the sugar beet plant cell with the nucleic acid construct, and possibly regenerating the transgenic sugar beet plant from the transformed sugar beet plant cell.

The present invention is also related to the obtained (recovered) transgenic plant or the transgenic plant cell resistant to an infection by a virus comprising a TGB-3 sequence, preferably one of the viruses described in the enclosed Table 1, more preferably the BNYVV virus, said plant or plant cell comprising a nucleic acid construct having a TGB-3 modified nucleic acid sequence, being operably linked to one or more regulatory sequences capable of being active into a plant or a plant cell.

Preferably, said modified nucleic acid sequence is selected from the group consisting of SEQ ID NO 1, SEQ ID NO 3 and SEQ ID NO 5, being operably linked to one or more regulatory sequences active into a plant or a plant cell.

Preferably, the cell is a stomatal cell and the regulatory sequence comprises a promoter sequence and a terminator sequence capable of being active into a plant. Said promoter sequence can be constitutive or could be obtained from a foreign promoter sequence, and is preferably selected from the group consisting of the 35S Cauliflower Mosaic Virus promoter, and/or the polyubiquitin *Arabidopsis thaliana* promoter.

Advantageously, the promoter sequence is a root specific promoter, which is mainly capable of being active in the root tissue of plants, in particular sugar beet plants, such as the par promoter or the hemoglobin gene from *Perosponia andersonii*.

A further aspect of the present invention is related to a transgenic plant tissue such as fruit, stem, root, tuber, seed of the transgenic plant according to the invention or a reproducible structure (preferably selected from the group consisting of calluses, buds or embryos) obtained from the transgenic plant or the plant cell according to the invention.

The techniques of plant transformation, tissue culture and regeneration used in the method according to the invention are the ones well known by the person skilled in the art. Such techniques are preferably the ones described in the International Patent Applications WO95/101778, WO91/13159 (corresponding to the European Patent Application EP-B-0517833), WO98/07875, which are incorporated herein by reference. Guard cell protoplasts are the preferred tissues for transformation of sugar beet plants.

These techniques are preferably used for the preparation of transgenic sugar beet plants and plant cells according to the invention.

Amongst sugar beet plants transformed with the mutated or genetically modified TGB-3 (P15) sequences according to the invention (SEQ ID NOS: 1, 3 and 5), plants were found that clearly displayed strong resistance to BNYVV in bioassays and these findings were confirmed in field trials. Strong BNYVV resistance was in particular found amongst plants transformed with SEQ ID NO: 3.

The production of a mutated P15 protein appears to be triggering the resistance. Western blot analysis demonstrated that the expression of mutated P15 protein in highly resistant plants, transformed with SEQ ID NO: 3, was strongly reduced but nevertheless still present, indicating that the obtained silencing mechanism was not yet efficient enough to degrade every P15 mRNA.

The quantity of p15 produced by transgenic plants overproducing p15 which are not silenced by PTGS was compared to the quantity of p15 produced by resistant plants wherein the PTGS mechanism is active.

A more detailed molecular characterization of the plant material demonstrated the presence of small RNA molecules complementary to both the sense and the anti-sense strands of the BNYVV TGB-3 (P15) WT sequence. It is generally believed that the presence of these sense and antisense small RNAs are undeniably linked to a post-transcriptional gene silencing (PTGS) induced resistance mechanism.

Northern blot analysis of resistant plants infected with the BNYVV virus confirmed the absence of the BNYVV RNA2 as compared to susceptible controls. Due to the high homology-dependent sequence specificity of the small P15 RNA molecules generated in the resistant plants, these transcripts activate the degradation process of the whole (entire) RNA2.

In these plants a PTGS mechanism was generated without being triggered by the genetic construct per se, more likely resulting from the rearrangements of the insertions.

The Inventors have discovered unexpectedly that hairpin constructs with the mutated TGB-3 (p15) sequences according to the invention or fragments thereof in sense and antisense orientation can efficiently trigger PTGS, targeting the degradation of the RNA2 of e.g. BNYVV. Especially the TGB-3 mutated sequence of SEQ ID NO 3 (possibly further modified e.g. to inhibit translation) and fragments or parts thereof proved very efficient in triggering PTGS in a highly reproducible manner.

Yet a further aspect according to the invention therefore relates to these double-stranded self-complementary RNA molecules, to nucleic acid constructs, in particular DNA constructs or nucleotidic sequences, vectors or expression cassettes for their expression in plant cells, to methods and uses based thereon.

Provided in the present invention is a nucleic acid construct, in particular a DNA construct, altering the expression of a TGB-3 movement protein, said nucleic acid construct comprising a first DNA sequence capable of "expressing" in a cell a sense fragment of a mutated BNYVV TGB-3 having e.g. (a modified) SEQ ID NO: 1, 3 or 5, or a fragment or part of (said modified) SEQ ID NO: 1, 3 or 5, and a second DNA sequence capable of "expressing" in said cell an antisense sequence of said mutated BNYVV TGB-3 having (a modified) SEQ ID NO: 1, 3 or 5 or a part or fragment of (said modified) SEQ ID NO: 1, 3 or 5. By "expression" is meant primarily "transcription" or the "generation of an (m)RNA fragment" (see next paragraph). Transcription may be followed by "translation". Yet, preferably translation is inhibited (see infra). By '(modified)' is meant that the sequence in question may be further modified, e.g. to inhibit translation. The term "SEQ ID NO: 3" for instance is meant to refer to SEQ ID NO: 3 as such, as well as to "modified" SEQ ID NO: 3 sequences such as SEQ ID NO: 10.

Provided in the present invention is as such a genetically modified TGB-3 viral sequence comprising the sequence of (a modified) SEQ ID NO: 3 or a fragment thereof, and comprising an antisense sequence of the said (modified) SEQ ID NO 3 or an antisense sequence of the said (modified) SEQ ID NO 3 fragment, wherein the TGB-3 viral sequence when transcribed in a cell is capable of forming a double-stranded self-complementing RNA molecule. Provided is e.g., a genetically modified TGB-3 viral sequence comprising a sequence selected from the group consisting of (a) a nucleotide sequence comprising SEQ ID NO: 3 and an antisense sequence of SEQ ID NO: 3; (b) a nucleotide sequence comprising a fragment of SEQ ID NO: 3 and an antisense sequence of said fragment of SEQ ID NO: 3; (c) a nucleotide sequence comprising a modified SEQ ID NO: 3 and an antisense sequence of said modified SEQ ID NO: 3; and (d) a nucleotide sequence comprising modified SEQ ID NO:3 fragment and an antisense sequence of said modified SEQ ID NO: 3 fragment; wherein said genetically modified TGB-3 viral sequence when transcribed in a cell is capable of forming a double-stranded self-complementing RNA molecule.

Preferably the sense and antisense sequences are comprised in one single nucleic acid sequence, one single DNA strand or molecule. Yet, they may be present in or on two different nucleic acid sequences, DNA strands or molecules that can base-pair and form thereby a double-stranded self-complementary RNA molecule.

When transcribed, the genetically modified TGB-3 viral sequence according to the invention yields an RNA molecule with a nucleotide sequence or nucleic acid sequence comprising 1) a sense nucleotide sequence of at least about 10 consecutive nucleotides (nt), preferably at least about 15, 20 more preferably at least about 50, 100, 150, 200, 250, 300, 350, or even more preferably about 400 consecutive nucleotides (nt)—e.g. the sequence of (the modified) SEQ ID NO: 3 or a fragment thereof—having between about 75 and about 100% sequence identity with at least part of the p15 BNYVV WT sequence (SEQ ID NO: 7), and 2) an antisense nucleotide sequence that is sufficiently complementary to this sense nucleotide sequence. As such, the RNA molecule that is expressed (transcribed and preferably not translated) is capable of forming a double-stranded self-complementary RNA molecule when expressed (transcribed) in sufficient amounts, such as an artificial hairpin RNA structure, with a double-stranded RNA stem by base-pairing between the regions with sense and antisense nucleotide sequence. By "sufficient amounts" is meant an amount that suffices to induce PTGS, preferably to induce a complete gene silencing.

The self-complementary hairpin constructs according to the invention are also referred to as mutated (BNYVV) p15 hairpin constructs (hp15).

Preferably the sense and antisense nucleotide sequences are each others complement. Desirably, there is less than about 50% mismatch between the sense and antisense RNA fragments in the complementary region, more desirably less than about 30% mismatch, preferably less than about 20% mismatch, more preferably less than about 10% mismatch, yet more preferably less than about 5, 4, 3, 2 or 1% mismatch.

Preferably the total length of the sense nucleotide sequence or DNA sequence is at least about 10 nt, 15 nt, yet more preferably at least about 20 nt, 25 nt particularly at least about 50 nt, more particularly at least about 100 nt, especially at least about 150 nt, more especially at least about 200 nt, 250 nt, 300 nt, quite especially at least about 350 nt or about 400 nt.

It will be appreciated that the longer the total or entire length of the sense nucleotide sequence is, the less stringent the requirements become for sequence identity between the total or entire sense nucleotide sequence (in this case in particular a sequence corresponding to SEQ ID NO 3 or part thereof) and the corresponding sequence in the target gene (in this case e.g. the BNYVV P15 WT sequence). Preferably, the sense nucleotide sequence should have a sequence identity over its entire length of at least about 75% with the BNYVV P15 WT sequence or part thereof, particularly of at least about 80%, more particularly of at least about 85%, quite particularly of about 90%, especially of about 95%, more especially of about 99% or even more (yet preferably less than 100%). The preferred mutated TGB-3 sequence, p15-ala4 (SEQ ID NO: 3), has three mutated bases compared to WT p15, which corresponds to a 99.24% homology or sequence identity. Another preferred sequence according to the invention, SEQ ID NO: 10, has five mutated bases compared to WT p15, which corresponds to a 98.74% homology or sequence identity (see FIG. 8).

However, it is preferred that the sense nucleotide sequence always includes a sequence of about 10 consecutive nucleotides, particularly of about 20 nt, more particularly of about 50 nt, especially about of 100 nt, quite especially of about 150 nt with 100% sequence identity to the corresponding part of the target nucleic acid (the BNYVV WT P15 sequence in this case). Preferably, for calculating the sequence identity and designing the corresponding sense nucleotide sequence, the number of gaps should be minimized, particularly for the shorter sense nucleotide sequences.

Preferably the modified sense TGB-3 sequence comprises at least the following modifications compared to the WT (wild type) P15 sequence: the WT P15 gene is mutated at nucleic acid position 3 in which G is replaced by C, another specific substitution comprises the mutation of nucleic acid position 158 in which A is replaced by C, further specific substitutions are directed to mutations at positions 160 and 161 in which AG are replaced by GC plus the additional mutation at position 397 in which T is replaced by C (SEQ ID NO: 10, see also FIG. 8). Such modification at position 3 inhibits a translation initiation and the modification at position 397 destroys the translation stop signal. Another preferred modified sense TGB-3 sequence according to the invention is SEQ ID NO 3 which contains the following modifications compared to the WT p15 gene: a mutation of nucleic acid position 158 in which A is replaced by C, and further specific substitutions directed to mutations at positions 160 and 161 in which AG are replaced by GC.

The length of the antisense nucleotide sequence is largely determined by the length of the sense nucleotide sequence, and will preferably correspond to the length of the latter sequence. However, it is possible to use an antisense sequence which differs in length by about 10% to about 50%, more preferably by about 10% to about 15% from the sense nucleotide sequence.

Similarly, the nucleotide sequence of the antisense region is largely determined by the nucleotide sequence of the sense region, and preferably is identical to the complement of the nucleotide sequence of the sense region. Particularly with longer antisense regions, it is however possible to use antisense sequences with lower sequence identity to the complement of the sense nucleotide sequence, preferably with at least about 75% sequence identity, more preferably with at least about 80%, particularly with at least about 85%, more particularly with at least about 90% sequence identity, especially with at least about 95% sequence to the complement of the sense nucleotide sequence.

Nevertheless, it is preferred that the antisense nucleotide sequence always includes a sequence of about 10, about 15 consecutive nucleotides (nt), preferably of about 20 nt, more preferably of about 50 nt, especially of about 100 nt, quite especially of about 150 nt with 100% sequence identity to the complement of a corresponding part of the sense nucleotide sequence. It is clear that the length of the stretch of the consecutive nucleotides with 100% sequence identity to the complement of the sense nucleotide sequence cannot be longer than the sense nucleotide sequence itself. Again, preferably the number of gaps should be minimized, particularly for the shorter antisense sequences. Further, it is also preferred that the antisense sequence has between about 75% to 100% sequence identity with the complement of the target sequence.

The order of the sense and antisense nucleotide sequences in the nucleotide sequences or DNA constructs according to the invention is thought not to be critical.

Preferably the sense and antisense sequences in the modified TGB-3 viral sequence according to the invention are interspersed by a linker or spacer nucleotide sequence, which preferably is an intron. This intron preferably is a plant intron, more preferably a (sugar) beet intron. Preferably an intron of highly transcribed genes, more preferably of highly transcribed sugar beet genes, is used. Preferably, the highly transcribed genes are ribosomal RNA genes (24, 25).

Preferably the sense TGB-3 fragment in the genetically modified TGB-3 sequence according to the invention comprises (a modified) SEQ ID NO: 1, 3 or 5, or parts or fragments thereof. For instance the genetically modified TGB-3 viral sequence according to the invention may comprise at least nt 100 to nt 399, nt 150 to nt 399, or nt 163 to nt 399 of (modified) SEQ ID NOs: 1, 3 or 5.

Most preferably, the sense TGB-3 fragment in the genetically modified TGB-3 sequence according to the invention comprises (a modified) SEQ ID NO: 3 or parts or fragments thereof. For instance the genetically modified TGB-3 viral sequence according to the invention may comprise at least nt 100 to nt 399, nt 150 to nt 399, or nt 163 to nt 399 of (a modified) SEQ ID NO: 3. Even more preferred, the sense TGB-3 fragment in the DNA construct according to the invention consists of (a modified) SEQ ID NO: 3 or parts thereof, for instance it may consist of at least nt 100 to nt 399, nt 150 to nt 399, or nt 163 to nt 399 of (a modified) SEQ ID NO: 3.

Advantageously, the sense TGB-3 fragment in the genetically modified TGB-3 sequence according to the invention is further mutated to contain at least one translation stop codon with the aim of inhibiting translation. Advantageously, the stop codon(s) of said sense TGB-3 fragment in the genetically modified TGB-3 sequence according to the invention is destroyed. The translation start codon may also be modified to inhibit translation initiation. The ATG start codon of SEQ ID NO: 3 was for instance modified into ATC and the TAA stop codon was modified into CAA (see FIG. 8). This particular sequence is referred to as a "modified" SEQ ID NO: 3. The person skilled in the art can think of many other possibilities.

Preferred constructs according to the invention are DNA constructs or nucleotide sequences wherein the sense TGB-3 fragment in the genetically modified TGB-3 viral sequence according to the invention comprises SEQ ID NO: 10. Even more preferred are DNA constructs wherein the sense TGB-3 fragment in the genetically modified TGB-3 sequence according to the invention consists of SEQ ID NO: 10.

Preferred genetically modified TGB-3 sequences according to the invention comprise SEQ ID NO: 9 or 13. Even more preferred are genetically modified TGB-3 sequences that consist of SEQ ID NO: 9 or 13.

Advantageously, the genetically modified TGB-3 viral sequence according to the invention is operably linked to a promoter, preferably a heterologous promoter that is active in the roots. Preferred promoter sequences active in the root tissue of plants are the par promoter and the hemoglobin gene from *Perosponia andersonii*. Most preferred are beet root specific promoters that are active in the roots of a beet plant. Optionally a DNA region involved in transcription termination and/or polyadenylation or other regulatory sequences (e.g. sequences that enhance transcription) may be operably linked to the DNA construct according to the invention.

As such, the invention further relates to a vector, in particular an expression vector or expression cassette, comprising a genetically modified TGB-3 sequence according the invention, operably linked with one or more regulatory sequences.

The present invention further relates to a double-stranded self-complementary RNA molecule expressed by a genetically modified TGB-3 sequence according to the invention or by a vector or expression cassette according the invention.

Another aspect according to the invention concerns a host cell transformed with a genetically modified TGB-3 sequence according to the invention and/or with a vector according to the invention and/or with an RNA molecule according to the invention. The host cell preferably is a plant cell, more preferably a beet cell and most preferably a sugar beet cell.

The present invention further relates to a transformed plant, preferably a transformed beet plant, most preferably a transformed sugar beet plant, comprising in its genome a DNA construct and/or a vector according to the invention, and/or comprising in its cells an RNA molecule according to the invention.

Preferably a DNA construct comprising the genetically modified TGB-3 viral sequence according to the invention and/or a vector comprising same is used to transform plant material such as plant cells and/or plant tissues. Preferably the modified TGB-3 sequence according to the invention is stably integrated in the genome of a (plant) cell. Alternatively it may be present in episomal form.

The present invention thus also relates to transformed or genetically modified plant cells that comprise such a DNA construct and/or a vector and/or an RNA molecule according to the invention. It is also possible to use the RNA molecules according to the invention per se to confer BNYVV resistance or tolerance (see infra).

Another aspect of the present invention relates to a transgenic plant, preferably a sugar beet plant, regenerated from a host cell, preferably a plant cell, that is transformed with such a DNA construct, a vector and/or RNA molecule according to the invention and that exhibits an altered expression of a TGB-3 movement protein. Preferably the expression of the (BNYVV) TGB-3 (p15) molecule is strongly reduced compared to a control (not transformed or not transformed with a p15 hairpin construct according to the invention).

An example is here given for reduced BNYVV p15 expression. The BNYVV p15 expression in the presence of a p15 hairpin RNA molecule according to the invention should thus be lower than the expression in absence thereof, preferably be only about 25%, particularly only about 10%, more particularly be only about 5% of the expression in absence of the p15 hairpin RNA molecule according to the invention or of the genetically modified TGB-3 viral sequence encoding it.

Advantageously BNYVV p15 expression is reduced to a level that it is no longer detectable. Presence of the p15 protein can be detected by Western blotting using p15 antibodies. Alternatively, the levels of this protein can be determined via mass-spectrometry as well known in the art. Most preferably no p15 protein or protein parts are produced at all, meaning that all of its mRNA is being degraded or at least inactivated. Advantageously p15 WT gene expression from the virus is silenced in the plant cells and plants transformed with the methods or means according to the invention.

Advantageously there is no viral replication in a plant or plant cell transformed with a genetically modified TGB-3 viral sequence, DNA construct, vector or RNA molecule according to the invention.

Yet another aspect of the present invention relates to the progeny of transformed plants according to the invention that comprises in the genome of at least part of its cells a genetically modified TGB-3 viral sequence and/or a vector according to the invention, and/or that comprises in at least part of its cells an RNA molecule according to the invention. Preferably this material (the modified viral sequence, the vector and/or the RNA molecule) is present in substantially all the cells of the plant. Advantageously, the progeny of a transformed plant according to the invention exhibits an altered expression of a (BNYVV) TGB-3 movement protein. The same strategy can be applied to every virus listed in Table 1, however, the P15 sequence described here will only target the BNYVV virus. Examples of progeny are plant tissues like fruit, stem, root, tuber, and seed.

Yet another aspect according to the invention concerns seeds of a transformed plant, preferably a transformed sugar beet plant, according the invention.

The present invention also relates to (vegetatively) reproducible structures, such as calluses, buds, embryos, originating from a transformed plant according to the invention.

Advantageously this progeny, seeds, reproducible structures etc. comprise(s) in the genome of at least part of its cells, preferably in substantially all of its cells, a genetically modified TGB-3 viral sequence and/or a vector according to the invention and/or an RNA molecule according to the invention. Advantageously these plant materials may be regenerated into BNYVV resistant plants or plant materials.

Yet another aspect according to the invention relates to the use of such seeds or vegetatively reproducible structures for the regeneration therefrom of a plant, which preferably is a sugar beet plant, that is resistant against e.g. BNYVV and/or exhibits a much increased tolerance to BNYVV.

Yet another aspect according to the invention relates to a method to alter the expression of the whole of RNA2 and more in particular of a (BNYVV) TGB-3 movement protein in a plant or a plant cell, comprising the step of:
  introducing into the cells of a plant, which preferably is a sugar beet plant, a genetically modified TGB-3 viral sequence (DNA construct) and/or a vector comprising same according to the invention to obtain a transformed plant cell, wherein expression in said plant cells of an RNA molecule that is capable of forming a double-stranded RNA molecule alters the expression of the whole of RNA2 and more in particular of a (BNYVV) TGB-3 movement protein in said plant or plant cell and advantageously the expression of any other viral protein located on the same RNA in said plant or said cell.

Yet another aspect according to the invention relates to a method to induce post-transcriptional gene silencing of the whole of RNA2 and more in particular of a (BNYVV) TGB-3 movement protein in a plant or a plant cell, comprising the step of:
  introducing into the cells of a plant, which preferably is a sugar beet plant, a genetically modified TGB-3 viral sequence (DNA construct) and/or a vector comprising same according to the invention to obtain a transformed plant cell, wherein expression in said plant cells of an RNA molecule that is capable of forming a double-stranded RNA molecule triggers a mechanism of post-transcriptional gene silencing.

With a method of the invention as presented in the previous paragraphs the whole of RNA2 is advantageously degraded.

Still another aspect according to the invention concerns a method to render a plant or a plant cell resistant or more tolerant to a plant virus listed in Table 1, e.g. BNYVV, comprising the step of:
  introducing into the cells of a plant, which preferably is a sugar beet plant, a genetically modified TGB-3 viral sequence (DNA construct) and/or a vector comprising same according to the invention to obtain a transformed plant cell, wherein expression in said plant cells of an RNA molecule that is capable of forming a double-stranded RNA molecule is responsible for the resistance and/or increased tolerance of said plant to the plant virus, e.g. BNYVV.

Yet another aspect according to the invention relates to a method to induce extreme resistance in a plant or a plant cell, comprising the step of:
  introducing into the cells of a plant, which preferably is a sugar beet plant, a genetically modified TGB-3 viral sequence (DNA construct) and/or a vector comprising same according to the invention to obtain a transformed plant cell, wherein expression in said plant cells of an RNA molecule that is capable of forming a double-stranded RNA molecule is capable of inducing extreme resistance in plants that comprise a DNA construct and/or a vector according to the invention in at least part, preferably essentially all of its cells.

Still another aspect according to the invention relates to a method to (significantly) reduce or, block the spread of a virus [preferably one as described in Table 1 such as BNYVV] within a plant, comprising the step of:
  introducing into the cells of a plant, which preferably is a sugar beet plant, a genetically modified TGB-3 viral sequence (DNA construct) and/or a vector comprising same according to the invention to obtain a transformed plant cell, wherein expression in said plant cells of an RNA molecule that is capable of forming a double-stranded RNA molecule is capable of reducing or blocking the spread of the virus within the thus transformed plant or plant cell.

The spread of the virus may be reduced/blocked by reducing/blocking viral multiplication (in all or certain cell types), transport of the virus throughout the plant (e.g. by blocking long-distance transport or cell-to-cell movement), or by confining the spread of the virus to certain tissues only (e.g. to vascular parenchyma and not phloem cells).

Alternatively an RNA molecule according to the invention may be introduced in plant cells with the aim of altering the expression of a BNYVV TGB-3 movement protein, inducing post-transcriptional gene silencing of a TGB-3 movement protein, rendering a plant or a plant cell resistant or more tolerant to BNYVV, with the aim of inducing extreme resistance in a plant or a plant cell, or with the aim of blocking or reducing the spread of the virus in the plant.

A method according to the invention may further comprise the step of regenerating a transgenic plant from the transformed plant cell.

The methods of the invention comprise (at least) a step of preparing a suitable construct and of transforming the plant (cell) therewith to reach one of the above effects (see paragraph [0037]).

Plants transformed according to the invention advantageously were found to provide higher levels of resistance to BNYVV compared to natural sources of tolerance/resistance to the virus (such as the 'Rizor', 'Holly' or *Beta maritima* subsp. *maritima* accession WB42 sources of resistance well known in the art).

Plant transformation with a genetically modified TGB-3 sequence according to the invention, preferably one capable of forming a hairpin structure, appears to block and/or significantly reduce spread of the virus through the root system. Advantageously, the virus can hereby be prevented to reach the long-distance translocation system. Advantageously, plant transformation according to the invention prevents and/or significantly reduces virus multiplication in the cortex. The methods of the invention advantageously decrease the capacity of the virus to maintain an infectious potential in the soil.

The pathogen-derived resistance according to the invention further appeared different from that present in natural sources. Pathogen-derived resistance as such advantageously may be combined with natural resistance mechanisms.

Advantageously, the combination of different sources of resistance (natural and pathogen-derived) can lead to an (further) increased stability of the rhizomania resistant variety and can help to ensure a long-term resistance to one or more pathotypes (at least one pathotype).

BRIEF DESCRIPTION OF THE DRAWINGS

FIGS. 1A and B represents a genetically modified TGB-3 viral sequence according to the invention (FIGS. 1A and B, SEQ ID NO: 9) with a sense mutated p15 nucleotide sequence (SEQ ID NO: 10, modifications compared to the WT in bold underlined herein) and an antisense p15 nucleotide sequence (bold italic, SEQ ID NO: 12) interspersed with an intron sequence of 91 bp (bold underlined, SEQ ID NO: 11). A few nucleotides in FIG. 1B are indicated in italic (double underlined). These do not belong to p15 nor to the intron but are still present as these are the remains of the cloning strategy, enclosing restriction sites. A construct comprising SEQ ID NO: 9 is also referred to as hp15 construct 2.

FIGS. 2A and B represents a genetically modified TGB-3 viral sequence according to the invention (FIGS. 2A and B, SEQ ID NO: 13) with a sense mutated p15 nucleotide sequence and an antisense p15 nucleotide sequence (bold italic) interspersed with an intron sequence of 550 bp (bold underlined, SEQ ID NO: 14). A few nucleotides in FIG. 2bB are indicated in italic (double underlined). These do not belong to p15 nor to the intron but are still present as these are the remains of the cloning strategy, enclosing restriction sites. The sense and antisense p15 nucleotide sequences herein are the same as those given in FIG. 1B. A construct comprising SEQ ID NO 13 is also referred to as hp15 construct 3.

FIG. 3 represents the WT p15 sequence (SEQ ID NOs: 7 and 8).

FIG. 8 highlights the differences in SEQ ID NO 10: compared to a WT p15 BNYVV sequence represented by SEQ ID NO: 7.

DETAILED DESCRIPTION OF THE PREFERRED EMBODIMENT

Figure 4:
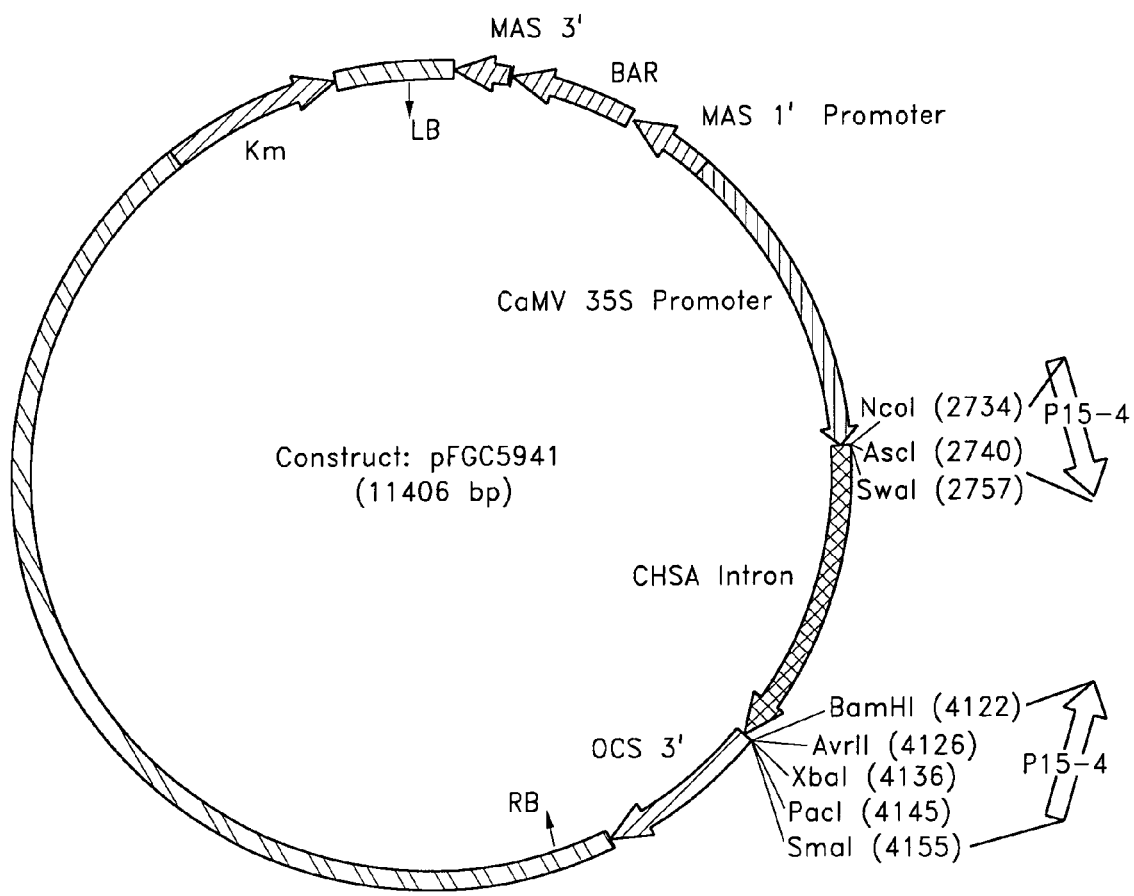
FIG. 4 is a schematic representation of the pFGC5941 vector into which the BNp15-ala4 gene was introduced in sense and antisense orientation, interspersed by an intronic sequence of the Chalcone Synthase A gene of petunia (CHSA). CaMV 35S promoter: promoter 35S of CaMV; OCS3: polyadenylation signal of the octopine synthase gene; MAS3: polyadenylation signal of the mannopine synthase gene; BAR: Basta herbicide resistance gene; Km: Kanamycine resistance gene; RB, LB: left and right t-DNA borders.

In a preferred embodiment according to the invention the sense and antisense modified TGB-3 nucleotide sequence are comprised in one molecule, meaning that the sense mutated TGB-3 RNA fragment and the antisense mutated TGB-3 RNA fragment are comprised in one single RNA molecule. Advantageously, the RNA molecule according to the invention is capable of folding such that said RNA fragments comprised therein form a double-stranded hairpin RNA molecule.

As used herein "hairpin RNA" refers to any self-annealing double stranded RNA molecule. In its simplest representation, a hairpin RNA consists of a double stranded stem made up by the annealing RNA strands, connected by a single stranded RNA loop, and is also referred to as a "pan-handle RNA". However, the term "hairpin RNA" is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software such as FOLDRNA (23).

Alternatively the sense and antisense modified TGB-3 nucleotide sequences may be present in or on two separate molecules or nucleotide sequences, which may be administered or provided to a plant cell simultaneously and/or consecutively, preferably with not too much time passing between the first and second nucleotide sequence being provided so that, when transcribed, a double-stranded RNA molecule can form by base-pairing.

Preferably, the DNA sequences according to the invention are stably integrated in the genome of the plant cell being transformed with the genetically modified TGB-3 viral sequences according to the invention and/or with a vector comprising these.

Alternatively, the transgene comprising a genetically modified TGB-3 viral sequence according to the present invention may be located on an episome or a self-replicating vector. Examples of self-replicating vectors are viruses, in particular gemini viruses.

A genetically modified TGB-3 viral sequence according to the present invention may also be directly transformed into the plastid genome. Plastid transformation technology is extensively described in U.S. Pat. Nos. 5,451,513; 5,545,817 and 5,545,818, in PCT application no. WO 95/16783, and in McBride et al. 1994 *PNAS USA* 91:7301-7305, which are incorporated by reference herein. The basic technique for chloroplast transformation involves introducing regions of cloned plastid DNA flanking a selectable marker together with the nucleotide sequence of interest into a suitable target tissue, using for instance biolistics or protoplast transformation (for instance calcium chloride or PEG-mediated transformation). The 1 to 1.5 kb flanking regions facilitate homologous recombination with the plastid genome and thus allow the replacement or modification of specific regions of the plastome.

Methods for transformation and for regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells.

Numerous transformation vectors available for plant transformation are known to those of ordinary skill in the art, and the DNA or nucleotide constructs according to this invention (comprising the genetically modified TGB-3 viral sequence) can be used in conjunction with any such vectors. The selection of vector depends upon the preferred transformation technique.

Selection markers used routinely in transformation include the nptII gene, which confers resistance to kanamycin and related antibiotics (Messing & Vierra 1982 *Gene* 19:259-268; Bevan et al. 1983 *Nature* 304:184-187), the bar gene, which confers resistance to the herbicide phosphinothricin (White et al. 1990 *Nucl. Acids Res.* 18:1062; Spencer et al. 1990 *Theor. Appl. Genet.* 79:625-631), the hph gene, which confers resistance to the antibiotic hygromycin (Blochinger & Diggelmann *Mol. Cell Biol.* 4:2929-2931), the dhfr gene, which confers resistance to methotrexate (Bourouis et al. 1983 *EMBO J.* 2:1099-1104), the EPSPS gene, which confers resistance to glyphosate (U.S. Pat. Nos. 4,940,935 and 5,188,642), the aac(6') gene encoding resistance to gentamycin (WO 94/01560), or the pat and imi genes well known in the art.

Many vectors are available for transformation or genetic modification of plant cells using *Agrobacterium tumefaciens*. These typically carry at least one T-DNA border sequence and include vectors such as pBIN19 (Bevan, 1984 *Nucl. Acids Res.*). Typical vectors suitable for *Agrobacterium* transformation include the binary vectors pCIB200 and pCIB2001, as well as the binary vector pCIB10 and hygromycin selection derivatives thereof (See, for example, U.S. Pat. No. 5,639,949). The advantage of the use of *Agrobacterium tumefaciens* techniques for plant transformation is the presence of a low copy number and minimal rearrangements compared to other techniques.

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. Transformation techniques that do not rely on *Agrobacterium* include transformation via direct gene transfer, particle bombardment, protoplast uptake (for instance PEG and electroporation), pollen-mediated transformation, plant RNA virus-mediated transformation, microinjection, the transformation of wounded and/or enzyme-degraded embryogenic tissues and/or immature embryos, liposome-mediated transformation, and the like. The choice of vector depends largely on the preferred selection for the species being transformed and the selection marker being used. Typical vectors suitable for non-*Agrobacterium* transformation include pCIB3064, pSOG19, and pSOG35 (See, for example U.S. Pat. No. 5,639,949, incorporated by reference herein).

The components of the expression system may be modified, for instance to increase expression of the sense and antisense RNA fragments.

"Expression cassette" as used herein means a DNA sequence capable of directing expression of a particular nucleotide sequence in an appropriate host cell, comprising a promoter operably linked to the nucleotide sequence of interest which is operably linked to termination signals.

The expression cassette comprising the nucleotide sequence of interest, in the present case a genetically modified TGB-3 viral sequence according to the invention, may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event.

The expression cassettes may also comprise any further sequences required or selected for the expression (and possibly the translation) of the transgene. Such sequences include e. g., but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described above. The following is a description of various components of typical expression cassettes.

"Regulatory elements" refer to sequences involved in conferring the expression of a nucleotide sequence. Regulatory elements usually comprise a promoter operably linked to the nucleotide sequence of interest and termination signals. They may also encompass sequences required for proper translation of the nucleotide sequence or interest. In the present case, translation of the sense nucleotide sequence of the genetically modified TGB-3 viral sequence is preferably inhibited, by modification of the presumed translation start and/or stop codon (see infra).

The expression of the nucleotide sequence in the expression cassette may be under the control of a constitutive promoter, or of an inducible promoter which initiates transcription only when the host cell is exposed to some particular external stimulus. In the case of a multicellular organism, such as a plant, the promoter can also be specific to a particular tissue or organ or stage of development.

The promoter operably linked to the sense and/or antisense nucleotide sequences according to the invention may be a native promoter of the cell to transform. The promoter alternatively can be a heterologous promoter, for example a tissue specific promoter, a developmentally regulated promoter, a constitutive promoter or an inducible promoter. Appropriate promoters are well known to person skilled in the art. In the present invention strong heterologous promoters that are active in root tissues or are primarily active therein (when expression in other tissues is not desired) are preferred.

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tm/terminator, the opaline synthase terminator and the pea rbcS E9 terminator and the like.

Numerous sequences have been found to enhance gene expression from within the transcriptional unit and these sequences can be used in conjunction with the genetically modified TGB-3 sequences of the invention to increase their expression in transgenic plants. For example, various intron sequences such as introns of the maize Adhl gene have been shown to enhance expression. In addition, a number of non-translated leader sequences derived from viruses are also known to enhance expression.

Preferably at least one "plant-expressible" promoter is operably linked to the sense nucleotide sequence and/or the antisense nucleotide sequence (see above). Preferably the sense and antisense nucleotide sequences in the genetically modified TGB-3 sequence according to the invention are under the control of the same promoter(s).

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell or tissue, i.e., certain promoters of viral or bacterial origin such as the CaMV35S, the subterranean clover virus promoter No 4 or No 7, or T-DNA gene promoters.

Below some options with respect to promoter choices and arrangements are described, depending on whether or not the genetically modified sense and antisense TGB-3 nucleotide sequences according to the invention are comprised in a single nucleotide sequence or DNA strand.

The sense and antisense nucleotide sequences in the genetically modified TGB-3 viral sequence according to the invention preferably are under the control of one single promoter, especially when both are comprised in one single nucleotide sequence. They may, however, also be each under the control of a different promoter (for instance when provided on 2 different sequences). I.e., the sense DNA sequence may be operably linked to a first promoter and the antisense DNA sequence operably linked to a second promoter. The first promoter and the second promoter may be the same promoter or may be different promoters. The promoter may be a divergent or bi-directional promoter capable of initiating transcription of DNA sequences on each side of the promoter.

When the sense RNA fragment and the antisense RNA fragment are comprised in or expressed as two RNA molecules (two separate RNA strands), the sense DNA sequence and the antisense DNA sequence may for instance be operably linked to a bi-directional promoter. Alternatively, the sense DNA sequence may be operably linked to a first promoter and the antisense DNA sequence operably linked to a second promoter. The first promoter and the second promoter may be the same promoter or may be different promoters.

The antisense sequence may be the complementary DNA strand of the sense modified TGB-3 sequence in said DNA molecule (in this case a DNA molecule having two strands). In this case, it is possible to have a promoter operably linked to said sense or said antisense DNA sequence, a first site-specific recombination site between said promoter and said sense or said antisense DNA sequence, and a second site-specific recombination site at the 3'-end of said sense or said antisense DNA sequence, wherein said first and second site-specific recombination sites are capable of inverting said first or second DNA sequence between said first and second site-specific recombination sites in presence of a site-specific recombinase. As a result of said inverting, said first promoter is then capable of expressing said antisense (or sense, depending on which DNA sequence was originally linked to the promoter) DNA sequence. The plant cell preferably further comprises a site-specific recombinase capable of recognizing said site-specific recombination sites.

The DNA construct or sequence according to the invention, apart from a sense and antisense modified TGB-3 viral nucleotide sequence, advantageously further comprises a linker or spacer nucleotide sequence between the DNA sequences encoding the sense and antisense RNA fragments.

In the absence of such a spacer sequence, the RNA molecule will still be able to form a double-stranded RNA, particularly if the sense and antisense nucleotide sequence are larger than about 10 nucleotides and part of the sense and/or antisense nucleotide sequence will be used to form the loop allowing the base-pairing between the regions with sense and antisense nucleotide sequence and formation of a double stranded RNA. It is expected that there are no length limits or sequence requirements associated with the spacer region, as long as these parameters do not interfere with the capability of the RNA regions with the sense and antisense nucleotide sequence to form a double stranded RNA. In a preferred embodiment, the spacer region varies in length from 5 to about 1000 bp.

In a preferred embodiment, the hairpin RNA formed by the sense and antisense region and if appropriate the spacer region, is an artificial hairpin RNA. By "artificial hairpin RNA" or "artificial stem-loop RNA structure", is meant that such hairpin RNA is not naturally occurring in nature.

A preferred spacer or linker nucleotide sequence is an intron sequence, preferably one in sense orientation, enhancing the efficiency of reduction of expression of the target nucleic acid, BNYVV p15 or BNYVV RNA2 in the present context. The enhancement in efficiency may be expressed as an increase in the frequency of plants wherein silencing occurs or as an increase in the level of reduction of BNYVV p15 or RNA2 expression.

Preferred intron nucleotide sequences are derived from plant genes, like presumed ribosomal RNA genes or highly transcribed plant genes. These introns may be derived from any plant gene, yet preferably are derived from dicotyledonous plant genes, e.g. from petunia genes, yet most preferably are derived from (sugar) beet genes. It is also possible to use only part of these (plant) introns, for instance at least the borders containing splicing signals (see below). The whole of these introns and parts thereof in the context of the invention are referred to as "intron fragments" or "intron sequences".

A preferred length for such intron nucleotide sequences is between about 5 and about 1000 bp, preferably between about 50 and about 600 bp, more preferably of between about 90 and about 550 bp. Preferred intron sequences comprise SEQ ID NO 11 or 14, or even more preferably consist of SEQ ID NO 11 or 14.

Intron processing depends on proper 5' and 3' splice junction sequences and at least these should be maintained of an intron sequence. Consensus sequences for these junctions have been derived for both animal and plant mRNAs, but only a few nucleotides are known to be invariant.

Both beet introns described infra (SEQ ID NOs 11 and 14) were found to be highly suitable, yet the shorter sequence performed slightly better than the longer sequence.

The RNA molecule, comprising the sense and antisense nucleotide sequences capable of forming for instance a hairpin structure, which are produced by the transcription of the chimeric genes, can also be introduced directly in a plant cell. Such RNA molecules could be produced e.g., by"

cloning the DNA region capable of being transcribed into an RNA molecule with a nucleotide sequence comprising a sense nucleotide sequence of at least 10 consecutive nucleotides having between 75 and 100% sequence identity with at least part of the nucleotide sequence of the nucleic acid of interest and an antisense nucleotide sequence including at least 10 consecutive nucleotides, preferably at least about 15 nt, 20nt, particularly at least about 50 nt, more particularly at least about 100 nt, especially at least about 150 nt, more especially at least about 200 nt, 250 nt, 300 nt, quite especially at least about 350 nt or about 400 nt, and having between about 75% to about 100% sequence identity with the complement of the at least about 10 consecutive nucleotides of the sense nucleotide sequence, whereby the RNA is capable of forming a double stranded RNA by basepairing between the regions with sense and antisense nucleotide sequence resulting for instance in a hairpin RNA structure, under control of a promoter suitable for recognition by a DNA dependent RNA polymerase in an in vitro transcription reaction, such as but not limited to a T7-polymerase specific promoter;

performing an in vitro transcription reaction by adding inter alia the suitable DNA-dependent RNA polymerase as well as the required reagents to generate the RNA molecules; and isolating the RNA molecules.

In vitro transcription methods as well as other methods for in vitro RNA production are well known in the art and commercial kits are available. Methods for direct introduction of RNA in plant cells are also available to the skilled person and include but are not limited to electroporation, microinjection and the like.

The invention also further provides: a BNYVV resistant or tolerant plant that comprises in the genome of at least part of its cells, preferably in substantially all of its cells, a genetically modified TGB-3 viral sequence according to the invention and/or a vector comprising same, which when transcribed yields an RNA molecule that triggers PTGS and the destruction of BNYVV RNA2 hereby. Also provided is a BNYVV resistant or tolerant plant that comprises in at least part of its cells, preferably in substantially all of its cells, an RNA molecule according to the invention to achieve the above-described effect.

A "plant" refers to any plant or part of a plant at any stage of development. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units. The latter are also referred to as (vegetatively) reproducible structures meaning that they may be regenerated into a whole plant.

The obtained transformed plant, plant tissues and plant material can be used in a conventional breeding and plant propagation or regeneration schemes to produce more transformed plants with the same characteristics (virus resistance or tolerance) or to introduce the DNA construct according to the present invention in other varieties of the same or a related plant species.

"Virus resistance or tolerance" means herein that a resistant or tolerant cell or plant is either not susceptible or has reduced susceptibility to one or more viruses as compared to a sensitive cell or plant. In the present case, resistance and preferably extreme resistance to BNYVV infections are envisaged. Resistance or tolerance for instance means that the usual symptoms of a virus infection, for instance BNYVV infection, are absent or reduced, or that accumulation or replication of the virus in the cell is prevented or reduced, or that movement of the virus, for instance from cell to cell is prevented or reduced.

The present invention relates to methods to regulate, i.e. to alter and preferably significantly reduce or even completely inhibit the expression of a viral (BNYVV) p15 RNA2 gene in cells, preferably plant cells, or plants. PTGS will inhibit the expression of every gene located on RNA2.

Commonly available methods were found to lack predictability. The present methods alleviate these problems and provide for reproducible and more efficacious regulation of viral resistance in plants.

The invention will now be further described by reference to the following detailed examples.

These examples are provided for purposes of illustration only, and are not intended to be limiting unless otherwise specified.

The principles demonstrated here for BNYVV and the BNYVV P15 apply equally well to the viruses listed in Table 1.

EXAMPLE 1

Characterization of BNYVV Resistant Transgenic Plants

Three independent transgenic *Beta vulgaris* lines were created that express the protein BNP15-Ala4 (encoded by SEQ ID NO 3). Two out of three lines were found resistant to BNYVV.

P15 protein expression was found to be significantly higher in the susceptible line than in the resistant lines. siRNAs were detected, but only in plants of the BNYVV resistant line (Table 2).

BNYVV resistance may thus be triggered by PGTS. To further test this hypothesis, one leaf of each line was infected with a viral inoculum (Stras 1234 providing RNA1, RNA2, RNA3 and RNA4). Few to no lesions developed on the leaves of resistant plants that were infected as such, whereas leaves of susceptible plants developed numerous lesions. P15-specific siRNA molecules were detected in plants of the BNYVV resistant lines, yet not in any of the susceptible plants.

No modification in the p15 gene sequence or in the sequence of the transcriptional terminator could be detected.

EXAMPLE 2

P15 Hairpin Constructs

To study the functionality of the PTGS inducing (mutated) P15 sequence, a binary *Agrobacterium* vector was constructed containing a genetically modified P15 gene (e.g., (a modified) SEQ ID NO 3) in sense and antisense orientation, interspersed by a petunia intron or a sugar beet intron.

Figure 5A:
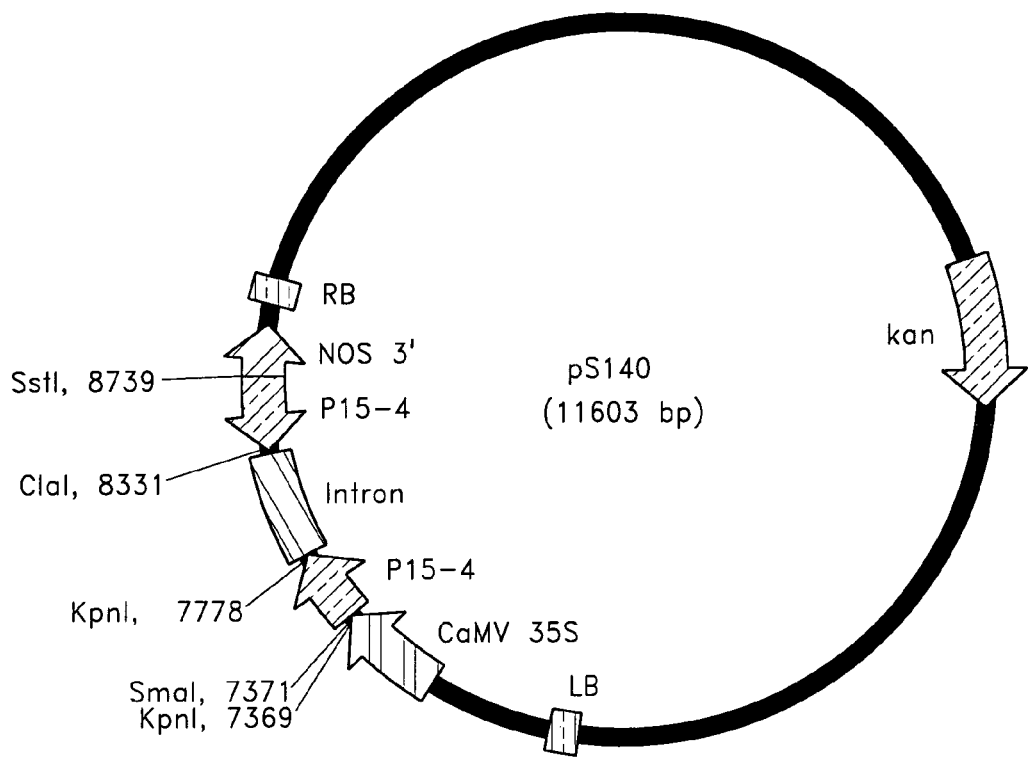
FIGS. 5A and B is a schematic representation of the pS140 and pS142 vectors into which the BNp15-ala4 gene was introduced in sense and antisense orientation, interspersed by a beet intronic sequence of 550 nt (FIG. 5A, pS140, construct 3) and 91 nt (FIG. 5B, pS142, construct 2), respectively. CaMV 35S promoter: promoter 35S of CaMV; NOS 3': nopaline synthase terminator; Kan: Kanamycine resistance gene; RB, LB: left and right t-DNA borders.
Figure 5B:
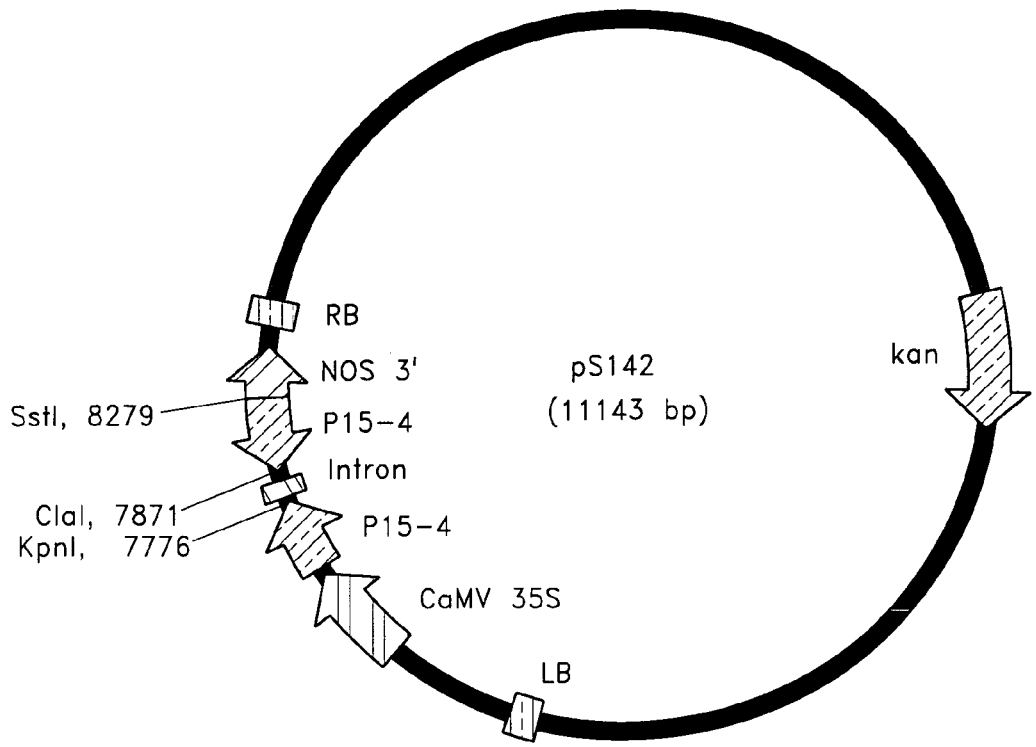

Below the results obtained with three hp15 constructs (see FIGS. 4, 5) are given. The intronic sequence in construct 1 is derived from petunia (see FIG. 4), whereas the intronic sequence in constructs 2 and 3 is derived from beet. Constructs 2 and 3 differ in length of the intron only: 550 nt in the case of the pS140 vector and 91 nt only in the case of the pS142 vector (FIGS. 5A and B respectively).

The creation of the DNA constructs according to the invention and the cloning of these constructs into *Agrobacterium tumefaciens* (e.g. a (disarmed) GV3101 strain) was performed according to methods and techniques well known in the art. The p15 sense and antisense fragments and the introns were generated by PCR including specific restriction sites at the ends. Mixed together with the vector backbone, only one recombination/insertion of the fragments was possible based on the compatibility of these specific sites at the end of the fragments. The right restriction site of fragment one was the same as the left restriction site of fragment two.

For each of the above constructs, a hairpin homologue containing (the first 400 nt of) a GFP sequence [instead of a genetically modified p15 sequence] was created and used as control (hairpin control, referred to as hpGF). A MA buffer (10 mM MgCl$_2$, 200 µM acetosyringon) further served as treatment control.

EXAMPLE 3

Experimental Protocols

Leaf material of *Tetragonia expensa*, *Beta macrocarpa* and *Beta vulgaris* (plants sustaining BNYVV artificial leaf inoculation) was agro-infiltrated followed by an infection of BNYVV (Stras 1234 or Stras 12 (providing RNA1 and RNA2). For the protocols, see below and for the constructs, see above.

The *Agrobacterium tumefaciens* carrying a hairpin construct is grown up overnight at 28° C. The cells are pelleted by centrifugation (15 min at 5000 g) and resuspended in 10 mM MgCl$_2$ buffer containing acetosyringone (200 µM) and the OD600 nm adjusted to 1. The cell suspension is kept at room temperature for 3 h before infiltration.

Agro-infiltration is performed by injecting the *Agrobacterium* solution into leaves of seedlings (of e.g. *Beta macrocarpa*, *Beta vulgaris*, *Tertragonia expansa*, *Nicotiana benthamina*, *Chenopodium quinoa*) at the 4 leaf stage. A 2 ml needle-less syringe, is pressed on the upper side of a needle-wounded leaf. Each leaf, except the cotyledons is infiltrated.

Four days after agro-infiltration, the treated leaves were infected by mechanical inoculation by rubbing onto previously carborundum dusted leaves with 10 to 25 µl of inoculation solution (1 µg viral RNA (Stras 1234 or Stras 12), macaloid 0.04%, potassium phosphate buffer 50 mM, pH 7.5).

| | |
|---|---|
| *Beta macrocarpa* | 10 µl inoculation solution/leaf |
| *Beta vulgaris* | 25 µl inoculation solution/leaf |
| *Tertragonia expansa* | 25 µl inoculation solution/leaf |
| *Nicotiana benthaminana* | 20 µl inoculation solution/leaf |

Leaves from *Beta macrocarpa*, *Beta vulgaris*, *Tertragonia expansa* and *Nicotiana benthamina* were treated as such (see above) and the presence of Rhizomania symptoms observed therein 10 to 13 dpi (days post inoculation).

EXAMPLE 4

Effect of the Expression of hp15 mRNA on the Multiplication of BNYVV

A: Constructs with the Petunia Intron

The following Examples describe some of the results obtained in beet using hp15 constructs according to the invention.

Figure 6:
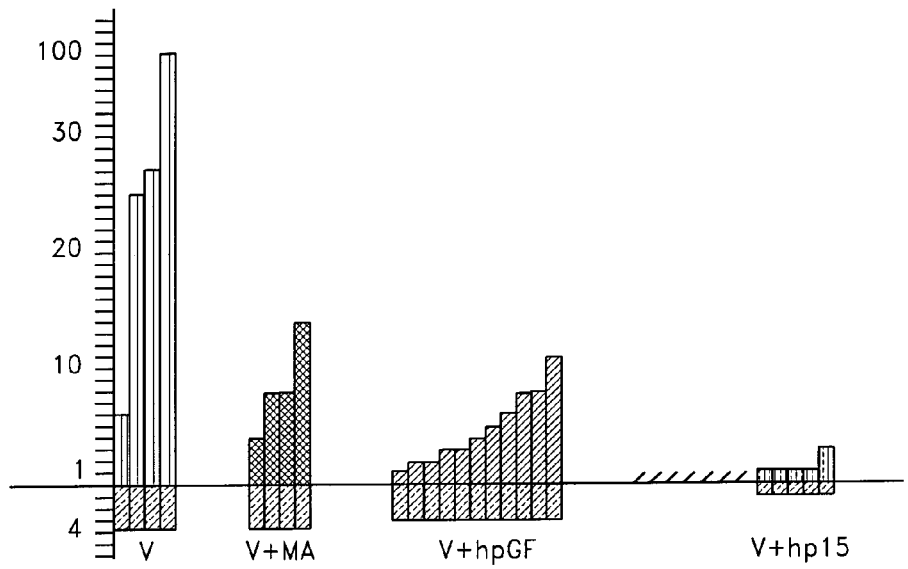
FIG. 6 is a statistical analysis of the PTGS data obtained with construct 1 (hp15 with the petunia intron). Each histogram represents the number (Y) and the size (−Y) of the lesions per infected leaf. /: no lesion; v: virus St1234, tp: buffer; hp: hairpin. In the Y axis: 1, 10, 20, 30, 100. In the −Y axis: 4. In the X-axis, from left to right: v; v+MA buffer; v+hpGF; v+hp15.

Results obtained with the construct 1 (FIG. 4) are summarized in FIG. 6. Yellow chlorotic lesions were observed on *Beta vulgaris* leaves that were agro-infiltrated with a suspension expressing the hpGF construct and on leaves infiltrated with the MA buffer. These lesions were similar to those observed on leaves that had not been infiltrated and inoculated.

No such lesions developed on leaves of plants that were agro-infiltrated with a suspension expressing the hp15 construct (construct 1). If any lesions were observed at all, they were much smaller and believed to correspond to zones where the leaf infiltration had not been optimal.

These preliminary results point out that hp15 constructs are suitable to induce PTGS in *B. vulgaris* plants and can induce BNYVV resistance.

B: Constructs with the Beet Intron

The above experiments were repeated with a higher number of beet plants and using constructs 2 and 3, which differ in the length of the intron only.

Figure 7:
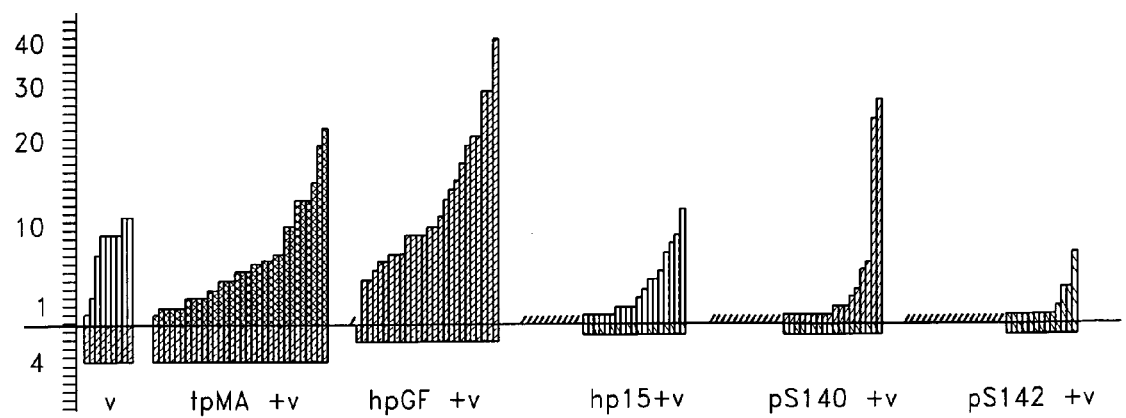
FIG. 7 is a statistical analysis of the PTGS data obtained with constructs 1, 2 and 3 respectively. Each histogram represents the number (Y) and the size (−Y) of the lesions per infected leaf. /: no lesion; v: virus St1234, tp: buffer; hp: hairpin; hp15: construct 1; pS140: construct 3; pS142: construct 2. In the Y axis: 1, 10, 20, 30, 40. In the −Y axis: 4. In the X-axis, from left to right: v; v+MA buffer; v+hpGF; v+hp15 (construct 1); v+pS140 (construct 3); v+pS142 (construct 2).

All leaves infiltrated with the MA buffer or with the *Agrobacterium tumefaciens* suspension expressing a hpGF homologue were found to exhibit a high number of lesions of about 3-4 mm in diameter. Leaves of plant agro-infiltrated with hp15 (constructs 2 or 3) developed no lesions at all, or a very low number of lesions of maximally 1 mm in diameter. The results represented in FIG. 7 indicate that construct 2 (with the beet intron of 91 nt) seems to confer a better protection against BNYVV.

C: Protection Against an Infection by a P-type Isolate.

The P type of BNYVV, found around Pithiviers in France, consists of five plus-sense RNAs. This isolate is highly pathogenic to beet plants. It is believed that the expression of a p26 protein worsens rhizomania symptoms (26).

The results described above (under section B) were repeated using a P-type BNYVV as viral inoculum.

No lesions were observed on leaves of plants agro-infiltrated with an *Agrobacterium tumefaciens* suspension expressing a hp15 construct.

Induction of PTGS by the intermediate of a hairpin construct thus seems to be a good source of resistance, against a viral infection, and in particular against BNYVV. Even against the most aggressive isolates plant resistance was obtained.

It is assumed that expression of the hp15 construct (in planta) results in the formation of dsRNA that is recognized and cut into pieces of about 21-23 nt (siRNA) by the enzyme Dicer. P15-specific siRNAs will form a complex with RISC (RNA induced silencing complex), that will on its turn target the RNA homologue, RNA2, and certain BNYVV subgenomic RNA species, and induce degradation of the latter. As such, the virus will no longer be able to move from one cell to another.

EXAMPLE 5 hp15 Constructs According to the Invention Block Viral Multiplication in the Cortical Cells Presence and spread of BNYVV (A, B, P-types) was studied in a susceptible diploid sugar beet breeding line 4D6834 ('4D'), in natural resistance sources (Holly-1-4 accession ('Ho') and *Beta vulgaris* ssp. *maritima* WB42 ('Bm')), and in beet plants transformed according to the invention.

In vascular tissues, the viral coat protein was observed within phloem sieve elements and vascular parenchyma. These observations support a long distance movement through the phloem. For detailed protocols on e.g., viral infection and immunodetection see Doucet, 2006, Ph.D. thesis, chapter 5, incorporated by reference herein.

The natural resistance sources like 'Ho' proved only partially resistant. Resistance of 'Ho' was for instance broken in the presence of high viral titers.

Resistant plants according to the invention and 'Bm' genotypes exhibited the same limitation of virus spread. An important difference between both, however, is that 'Bm' still enables the virus to multiply in the cortical cells. So, viral particles are still accessible to *P. betae* (the fungal vector), which appears to infect preferentially the cortex. The multiplication of the virus and consequently the maintenance of an infectious potential, even if to a lesser extend than in a susceptible variety, will be possible and a build-up of the infectious population will be maintained. The advantage of the resistant genotype according to the invention comes from its ability to prevent virus multiplication in the cortex. As compared to 'Bm', it will decrease the capacity of the virus to maintain an infectious potential in the soil.

EXAMPLE 6

General Conclusions

We can conclude from the above Examples that the pathogen-derived hp15 resistance according to the invention is highly efficient, even against the more aggressive BNYVV isolates.

The hp15 constructs of the invention successfully induced pathogen-derived plant resistance. The tested hp15 constructs all induced a degradation of RNA2 via PTGS.

The hpGF homologues never induced any PTGS mechanism (visual observation). Degradation of the BNYVV RNA2 was never observed in that case (Northern blot analysis).

The examples above relate to hp15 constructs containing a full length p15 sequence. Positive results were however also obtained when a fragment (a part or portion) of the p15 coding sequence was cloned into a suitable vector in the sense and antisense orientation. For instance, a construct that contained two thirds of the P15 BNYVV gene was also targeted by siRNAs (small interfering RNAs).

The above indicates that P15 hairpin constructs containing a genetically modified BNYVV TGB-3 sequence according to the invention or a part or fragment thereof, are highly suitable to induce PTGS, which will result in BNYVV resistant plants.

Transformed plants are preferably selected on the following criteria to maximize success. Transformants harboring a single copy construct are selected and the plants analyzed for their resistance to BNYVV infection. Plants producing high levels of small RNAs will show very high and robust levels of resistance. Agrobacterium transformation and/or plant transformation in accordance with the principles described in EP 1 174 513 are preferred as transformation technique since these techniques minimize rearrangements.

REFERENCES

1. Tamada T. & Baba T., *Annals of the Phytopathological Society of Japan* 39:325-332 (1973)
2. Kuszala M. & Putz C., *Annals of Phytopathology* 9:435-446 (1977)
3. Keskin B., *Archiv für Mikrobiology* 49:348-374 (1964)
4. Asher M. J. C., Rhizomania In *The sugar beet crop*, ed. D. A. Cooke and R. K. Scott, Chapman & Hall, London, pp. 312-338 (1993)
5. Richard-Molard M., Rhizomanie In *Institut francais de la betterave industrielle. Compte-rendu des travaux effectués en 1994*, ITB, Paris pp. 225-229 (1995)
6. Powell A. P. et al., *Science* 232:738-743 (1986)
7. Fritchen J. H. & Beachy R. N., *Ann. Rev. Microbiol.* 47:739-763 (1993)
8. Wilson T. M. A., *PNAS USA* 90, pp. 3134-3141 (1993)
9. Gonsalves D. & Slightom J. L., *Seminars in Virology* 4:397-405 (1993)
10. D'Halluin K. et al., *Biotechnology* 10:309-314 (1992)
11. Kallerhof J. et al., *Plant Cell Reports* 9:224-228 (1990)
12. Ehlers U. et al., *Theoretical and Applied Genetics* 81:777-782 (1991)
13. Kraus J. et al., Field performance of transgenic sugar beet plants expresing BNYVV coat protein plants, Fourth International Congress of Plant Molecular Biology, Int. Soc. for Plant Molecular Biology, Amsterdam (1994)
14. Maiss E. et al., Proceedings of the Third International Symposium on the Biosafety Results of Field Tests of Genetically Modified Plants and Microorganisms, Monterey, pp. 129-139 (1994)
15. Gilmer et al., *Virology* 189:40-47 (1992)
16. Bleykasten-Grosshans et al., *Mol. Plant-Microbe Interact.* 10:240-246 (1997)
17. Bouzoubaa et al., *J. Gen. Virol.* 67:1689-1700 (1986)
18. Richards & Tamada, *Annu. Revendication. Phytopathol.* 30:291-313 (1992)
19. Bouzoubaa et al., *J. Gen. Virol.* 68:615-626 (1987)
20. Herzog et al., *J. Gen. Virol.* 18:3147-3155 (1994)
21. Scott et al., *J. Gen. Virol.* 75:3561-3568 (1994)
22. Koonin & Dolja, *Crit. Revendication. Biochem. and Mol. Biol.* 28:375-430 (1993)
23. Zuker and Stiegler, *Nucl. Acids Res.* 9:133-148 (1981)
24. Higgins, *Encyclopedia of Life Sciences*, pp. 1-10 (2001)
25. Raska et al., *Biology of the Cell* 96:579-594 (2004)
26. Tamada et al., Proceeding of the 3$^{rd}$ symposium of the International Working Group on Plant Viruses with Fungal Vectors, American Society of Sugar Beet Technologists, Denver: p. 49 (1996)

TABLE 1

| Virus | Size of TGB-3 | Host | Reference |
| --- | --- | --- | --- |
| Apple stem pitting virus | 8 kDa | apple | Jelkman, 1994 J. Gen. Virol. 75: 1535-1542 |
| Blueberry scorch virus | 7 kDa | blueberry | Cavileer et al. 1994 J. Gen. Virol. 75: 711-720 |
| Potato virus M | 7 kDa | potato | Zavriev et al. 1991 J. Gen. Virol. 72: 9-14 |
| White clover mosaic virus | 8 kDa | clover | Forster et al. 1988 Nucl. Acids Res. 16: 291-303 |
| Cymbidium mosaic virus | 10 kDa | orchid | Neo et al. 1992 Plant Mol. Biol. 18: 1027-1029 |
| Potato virus X | 8 kDa | potato | Rupasov et al. 1994 J. Gen. Virol. 7: 1861-1869 |
| Barley stripe mosaic virus | 17 kDa | barley | Gustafson et al. 1986 Nucl. Acids Res. 14: 3895-3909 |
| Potato mop top virus | 21 kDa | potato | Scott et al. 1994 J. Gen. Virol. 75: 3561-3568 |
| Peanut clump virus | 17 kDa | peanut | Herzog et al. 1994 J. Gen. Virol. 75: 3147-3155 |
| Beet soil-borne virus | 22 kDa | Sugar beet | Koenig et al. 1996 Virology 216: 202-207 |

TABLE 2

Detection of P15 protein expression of P15-specific siRNAs in transgenic plants.

| Line N° | Sensitivity to BNVYY | P15 protein expression | SiRNA detection |
| --- | --- | --- | --- |
| 178 | R | + | + |
| 179 | R | + | + |
| 180 | S | ++ | − |

R: plant line resistant to BNYVV;
S: plant line sensible to BNYVV,
+: weak detection;
++: strong detection;
−: no detection

What is claimed is:

1. A genetically modified TGB-3 viral sequence comprising a sequence selected from the group consisting of
   (a) a nucleotide sequence comprising SEQ ID NO: 3 and an antisense sequence of SEQ ID NO: 3; and
   (b) a nucleotide sequence comprising a modified SEQ ID NO: 3 and an antisense sequence of said modified SEQ ID NO: 3, wherein the modification in SEQ ID NO: 3 consists of a modification that alters a start or a stop codon in SEQ ID NO: 3 so as to inhibit translation, wherein said genetically modified TGB-3 viral sequence when transcribed in a cell is capable of forming a double-stranded self-complementing RNA molecule.

2. The TGB-3 viral sequence of claim 1, wherein the sense and antisense sequences are comprised in one nucleic acid sequence.

3. The TGB-3 viral sequence of claim 2, further comprising an intron fragment interspersed between the sense and antisense sequences, wherein the TGB-3 viral sequence when transcribed in a cell is capable of forming a hairpin RNA molecule.

4. The TGB-3 viral sequence of claim 3, wherein the intron fragment is derived from a plant gene.

5. The TGB-3 viral sequence of claim 4, wherein the plant gene is a beet gene.

6. The TGB-3 viral sequence of claim 3, wherein the intron fragment is an intron fragment of highly transcribed genes.

7. The TGB-3 viral sequence of claim 6, wherein the highly transcribed genes are ribosomal RNA genes.

8. The TGB-3 viral sequence of claim 6, wherein the highly transcribed genes are highly transcribed sugar beet genes.

9. The TGB-3 viral sequence of claim 1 comprising SEQ ID NO: 9.

10. The TGB-3 viral sequence of claim 1 consisting of SEQ ID NO: 9.

11. A vector comprising the genetically modified TGB-3 viral sequence according to claim 1.

12. The vector of claim 11 operably linked to one or more regulatory sequence(s) active in a plant cell.

13. A double stranded self-complementary RNA molecule expressed by a vector of claim 11.

14. A transgenic plant or a transgenic plant cell resistant to a virus and comprising a nucleic acid construct having a genetically modified TGB-3 viral sequence according to claim 1 operably linked to one or more regulatory sequence(s) active in a plant or a plant cell.

15. The transgenic plant or transgenic plant cell according to claim 14, wherein the virus is the BNYVV virus.

16. The transgenic plant or transgenic plant cell according to claim 14, wherein said transgenic plant or transgenic plant cell comprises sugar beet.

17. The transgenic plant or transgenic plant cell according to claim 14, wherein the regulatory sequence comprises a promoter sequence or a terminator sequence that are active in a plant.

18. The transgenic plant of claim 17, wherein said promoter is active in the root tissue of plants.

19. The transgenic plant or transgenic plant cell according to claim 14, wherein said transgenic plant is sugar beet and said transgenic plant cell is a sugar beet cell.

20. The transgenic plant or transgenic plant cell according to claim 14, wherein the regulatory sequence(s) comprise a promoter sequence which is a constitutive or a foreign vegetal promoter sequence.

21. The transgenic plant or transgenic plant cell according to claim 20, wherein the promoter comprises the 35S Cauliflower Mosaic Virus promoter.

22. A transgenic plant tissue derived from the transgenic plant cell according to claim 14, wherein said tissue comprises said genetically modified TGB-3 viral sequence, and wherein said tissue is selected from the group consisting of fruit, stem, root, tuber, and seed.

23. A transgenic reproducible structure obtained from the transgenic plant cell according to claim 14, wherein said reproducible structure comprises said genetically modified TGB-3 viral sequence, and wherein said reproducible structure is selected from the group consisting of calluses, buds, and embryos.

24. A genetically modified TGB-3 viral sequence comprising a sequence selected from the group consisting of:
(a) a nucleotide sequence comprising a fragment of SEQ ID NO:3 and an antisense sequence of said fragment of SEQ ID NO:3; and
(b) a nucleotide sequence comprising a modified SEQ ID NO: 3 fragment and an antisense sequence of said modified SEQ ID NO: 3 fragment; wherein said fragment of SEQ ID NO:3 is about 25 nucleotides in length with 100% sequence identity to the corresponding part of SEQ ID NO:3, wherein the modification in SEQ ID NO: 3 consists of a modification that alters a start or a stop codon in SEQ ID NO: 3 so as to inhibit translation,
wherein said genetically modified TGB-3 viral sequence when transcribed in a cell is capable of forming a double-stranded self-complementing RNA molecule.

25. The TGB-3 viral sequence of claim 24, wherein a nucleic acid sequence comprises the sense and antisense sequences.

26. The TGB-3 viral sequence of claim 25, further comprising an intron fragment interspersed between the sense and antisense sequences, wherein the TGB-3 viral sequence when transcribed in a cell is capable of forming a hairpin RNA molecule.

27. The TGB-3 viral sequence of claim 26, wherein the intron fragment is derived from a plant gene.

28. The TGB-3 viral sequence of claim 27, wherein the plant gene is a beet gene.

29. The TGB-3 viral sequence of claim 26, wherein the intron fragment is an intron fragment of a highly transcribed gene.

30. The TGB-3 viral sequence of claim 29, wherein the highly transcribed gene comprises a ribosomal RNA gene.

31. The TGB-3 viral sequence of claim 29, wherein the highly transcribed gene comprises a highly transcribed sugar beet gene.

32. A vector comprising the genetically modified TGB-3 viral sequence according to claim 24.

33. The vector of claim 32, operably linked to one or more regulatory sequence(s) active in a plant cell.

34. A double stranded self-complementary RNA molecule expressed by a vector of claim 32.

35. A transgenic plant or a transgenic plant cell resistant to a virus and comprising a nucleic acid construct having a genetically modified TGB-3 viral sequence according to claim 24, operably linked to one or more regulatory sequence(s) active in a plant or a plant cell.

36. The transgenic plant or transgenic plant cell according to claim 35, wherein the virus is the BNYVV virus.

37. The transgenic sugar beet plant or transgenic sugar beet plant cell according to claim 35.

38. The transgenic plant or transgenic plant cell according to claim 35, wherein the regulatory sequence comprises a promoter sequence or a terminator sequence.

39. The transgenic plant of claim 38, wherein said promoter is active in the root tissue of a plant.

40. The transgenic plant or transgenic plant cell according to claim 35, wherein said transgenic plant is sugar beet and said transgenic plant cell is a sugar beet cell.

41. The transgenic plant, or transgenic plant cell according to claim 35, wherein the regulatory sequence(s) comprise a promoter sequence which is a constitutive or a foreign vegetal promoter sequence.

42. The transgenic plant or transgenic plant cell according to claim 41, wherein the promoter comprises the 35S Cauliflower Mosaic Virus promoter.

43. A transgenic plant tissue derived from the transgenic plant cell according to claim 35, wherein said tissue comprises said genetically modified TGB-3 viral sequence, and wherein said tissue is selected from the group consisting of fruit, stem, root, tuber, and seed.

44. A transgenic reproducible structure obtained from the transgenic plant cell according to claim 14, wherein said reproducible structure comprises said genetically modified TGB-3 viral sequence, and wherein said reproducible structure is selected from the group consisting of calluses, buds, and embryos.

45. A vector comprising the genetically modified TGB-3 viral sequence according to claim 9.

46. The vector of claim 45 operably linked to one or more regulatory sequence(s) active in a plant cell.

47. A double stranded self-complementary RNA molecule expressed by a vector of claim 45.

48. A transgenic plant or a transgenic plant cell resistant to a virus and comprising a nucleic acid construct having a genetically modified TGB-3 viral sequence according to claim 9 operably linked to one or more regulatory sequence(s) active in a plant or a plant cell.

49. The transgenic plant or transgenic plant cell according to claim 48, wherein the virus is the BNYVV virus.

50. The transgenic plant or transgenic plant cell according to claim 48, wherein said transgenic plant or transgenic plant cell comprises sugar beet.

51. The transgenic plant or transgenic plant cell according to claim 48, wherein the regulatory sequence comprises a promoter sequence or a terminator sequence that is active in a plant.

52. The transgenic plant or transgenic plant cell according to claim 48, wherein said transgenic plant is sugar beet and said transgenic plant cell is a sugar beet cell.

53. The transgenic plant or transgenic plant cell according to claim 48, wherein the regulatory sequence(s) comprise a promoter sequence which is a constitutive or a foreign vegetal promoter sequence.

54. The transgenic plant or transgenic plant cell according to claim 53, wherein the promoter comprises the 35S Cauliflower Mosaic Virus promoter.

55. A transgenic plant tissue comprising the genetically modified TGB-3 sequence of claim 9, wherein said tissue is derived from the transgenic plant cell according to claim 48, and wherein said tissue is selected from the group consisting of fruit, stem, root, tuber, and seed.

56. A transgenic reproducible structure comprising a genetically modified TGB-3 sequence of claim 9, wherein said genetically modified TGB-3 viral sequence when transcribed in a cell is capable of forming a double-stranded self-complementing RNA molecule, wherein said reproducible structure is obtained from the transgenic plant cell according to claim 48, and wherein said reproducible structure is selected from the group consisting of calluses, buds, and embryos.

57. A vector comprising the genetically modified TGB-3 viral sequence according to claim 10.

58. A nucleotide sequence comprising a modified SEQ ID NO: 3 and an antisense sequence of said modified SEQ ID NO: 3, wherein the modifications in SEQ ID NO: 3 consist of a modification which alters a start codon in SEQ ID NO: 3 so as to inhibit translation and a modification which alters a stop codon in SEQ ID NO: 3 so as to inhibit translation, wherein the nucleotide sequence when transcribed in a cell is capable of forming a double-stranded self-complementing RNA molecule.

* * * * *

UNITED STATES PATENT AND TRADEMARK OFFICE
CERTIFICATE OF CORRECTION

PATENT NO. : 7,663,024 B2 Page 1 of 1
APPLICATION NO. : 11/418384
DATED : February 16, 2010
INVENTOR(S) : Lauber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this

Twenty-eighth Day of December, 2010

David J. Kappos
*Director of the United States Patent and Trademark Office*

SEQUENCE LISTING

<160> NUMBER OF SEQ ID NOS: 14

<210> SEQ ID NO 1
<211> LENGTH: 399
<212> TYPE: DNA
<213> ORGANISM: Artificial Sequence
<220> FEATURE:
<223> OTHER INFORMATION: Genetically modified TGB-3 sequence: BNP15-Ala1
<220> FEATURE:
<221> NAME/KEY: CDS
<222> LOCATION: (1)..(399)

<400> SEQUENCE: 1

```
atg gtg ctt gtg gtt gca gta gct tta tct aat att gta

```
                   85                  90                  95
Val Thr Leu Thr Glu Thr Ile Phe Ile Ile Leu Ser Arg Leu Phe Gly
            100                 105                 110

Leu Ala Val Phe Leu Phe Met Ile Cys Leu Met Ser Ile Val Trp Phe
        115                 120                 125

Trp Tyr His Arg
    130

<210> SEQ ID NO 3
<211> LENGTH: 399
<212> TYPE: DNA
<213> ORGANISM: Artificial Sequence
<220> FEATURE:
<223> OTHER INFORMATION: Genetically modified TGB-3 sequence

```
Gly Cys Ile Met Ala Ala Asn Ser Phe Ala Gln Phe Gly Ser Cys Asp
         50                  55                  60

Ile Pro Lys His Val Ala Glu Ser Ile Thr Lys Val Ala Thr Lys Glu
 65                  70                  75                  80

His Asp Val Asp Ile Met Val Lys Arg Gly Glu Val Thr Val Arg Val
                 85                  90                  95

Val Thr Leu Thr Glu Thr Ile Phe Ile Ile Leu Ser Arg Leu Phe Gly
                100                 105                 110

Leu Ala Val Phe Leu Phe Met Ile Cys Leu Met Ser Ile Val Trp Phe
            115                 120                 125

Trp Tyr His Arg
    130

<210> SEQ ID NO 5
<211> LENGTH: 399
<212> TYPE: DNA
<213> ORGANISM: Artificial Sequence
<220> FEATURE:
<223> OTHER INFORMATION: Genetically modified TGB-3 sequence: BNP15-Asp9
<220> FEATURE:
<221> NAME/KEY: CDS
<222> LOCATION: (1)..(399)

<400> SEQUENCE: 5 atg gtg ctt gtg gtt aaa gta gat tta tct aat att gta ttg tac ata        48
Met Val Leu Val Val Lys Val Asp Leu Ser Asn Ile Val Leu Tyr Ile
 1               5                  10                  15 gtt gcc ggt tgt gtt gtt gtc agt atg ttg tac tca ccg ttt ttc agc        96
Val Ala Gly Cys Val Val Val Ser Met Leu Tyr Ser Pro Phe Phe Ser
            20                  25                  30 aac gat gtt aaa gcg tcc agc tat gcg gga gca att ttt aag ggg agc       144
Asn Asp Val Lys Ala Ser Ser Tyr Ala Gly Ala Ile Phe Lys Gly Ser
        35                  40                  45 ggc tgt atc atg gac agg aat tcg ttt gct caa ttt ggg agt tgc gat       192
Gly Cys Ile Met Asp Arg Asn Ser Phe Ala Gln Phe Gly Ser Cys Asp
     50                  55                  60 att cca aag cat gta gcc gag tcc atc act aag gtt gcc acc aaa gag       240
Ile Pro Lys His Val Ala Glu Ser Ile Thr Lys Val Ala Thr Lys Glu
 65                  70                  75                  80 cac gat gtt gac ata atg gta aaa agg ggt gaa gtg acc gtt cgt gtt       288
His Asp Val Asp Ile Met Val Lys Arg Gly Glu Val Thr Val Arg Val
                 85                  90                  95 gtg act ctc acc gaa act att ttt ata ata tta tct aga ttg ttt ggt       336
Val Thr Leu Thr Glu Thr Ile Phe Ile Ile Leu Ser Arg Leu Phe Gly
                100                 105                 110 ttg gat gat ttt ttg ttc atg ata tgt tta atg tct ata gtt tgg ttt       384
Leu Asp Asp Phe Leu Phe Met Ile Cys Leu Met Ser Ile Val Trp Phe
            115                 120                 125 tgg tat cat aga taa                                                   399
Trp Tyr His Arg
    130

<210> SEQ ID NO 6
<211> LENGTH: 132
<212> TYPE: PRT
<213> ORGANISM: Artificial Sequence
<220> FEATURE:
<223> OTHER INFORMATION: Genetically modified TGB-3 sequence

<400> SEQUENCE: 6

Met Val Leu Val Val Lys Val Asp Leu Ser Asn Ile Val Leu Tyr Ile
 1               5                  10                  15
```

```
Val Ala Gly Cys Val Val Ser Met Leu Tyr Ser Pro Phe Phe Ser
            20                  25                  30

Asn Asp Val Lys Ala Ser Ser Tyr Ala Gly Ala Ile Phe Lys Gly Ser
        35                  40                  45

Gly Cys Ile Met Asp Arg Asn Ser Phe Ala Gln Phe Gly Ser Cys Asp
    50                  55                  60

Ile Pro Lys His Val Ala Glu Ser Ile Thr Lys Val Ala Thr Lys Glu
65                  70                  75                  80

His Asp Val Asp Ile Met Val Lys Arg Gly Glu Val Thr Val Arg Val
                85                  90                  95

Val Thr Leu Thr Glu Thr Ile Phe Ile Ile Leu Ser Arg Leu Phe Gly
            100                 105                 110

Leu Asp Asp Phe Leu Phe Met Ile Cys Leu Met Ser Ile Val Trp Phe
            115                 120                 125

Trp Tyr His Arg
        130

<210> SEQ ID NO 7
<211> LENGTH: 399
<212> TYPE: DNA
<213> ORGANISM: Beet necrotic yellow vein virus
<220> FEATURE:
<221> NAME/KEY: CDS
<222> LOCATION: (1)..(399)
<223> OTHER INFORMATION: WT p15 sequence

<400> SEQUENCE: 7 atg gtg ctt gtg gtt aaa gta gat tta tct aat att gta ttg tac ata        48
Met Val Leu Val Val Lys Val Asp Leu Ser Asn Ile Val Leu Tyr Ile
1               5                   10                  15 gtt gcc ggt tgt gtt gtt gtc agt atg ttg tac tca ccg ttt ttc agc       96
Val Ala Gly Cys Val Val Val Ser Met Leu Tyr Ser Pro Phe Phe Ser
            20                  25                  30 aac gat gtt aaa gcg tcc agc tat gcg gga gca att ttt aag ggg agc      144
Asn Asp Val Lys Ala Ser Ser Tyr Ala Gly Ala Ile Phe Lys Gly Ser
        35                  40                  45 ggc tgt atc atg gac agg aat tcg ttt gct caa ttt ggg agt tgc gat      192
Gly Cys Ile Met Asp Arg Asn Ser Phe Ala Gln Phe Gly Ser Cys Asp
    50                  55                  60 att cca aag cat gta gcc gag tcc atc act aag gtt gcc acc aaa gag      240
Ile Pro Lys His Val Ala Glu Ser Ile Thr Lys Val Ala Thr Lys Glu
65                  70                  75                  80 cac gat gtt gac ata atg gta aaa agg ggt gaa gtg acc gtt cgt gtt      288
His Asp Val Asp Ile Met Val Lys Arg Gly Glu Val Thr Val Arg Val
                85                  90                  95 gtg act ctc acc gaa act att ttt ata ata tta tct aga ttg ttt ggt      336
Val Thr Leu Thr Glu Thr Ile Phe Ile Ile Leu Ser Arg Leu Phe Gly
            100                 105                 110 ttg gcg gtg ttt ttg ttc atg ata tgt tta atg tct ata gtt tgg ttt      384
Leu Ala Val Phe Leu Phe Met Ile Cys Leu Met Ser Ile Val Trp Phe
            115                 120                 125 tgg tat cat aga taa                                                   399
Trp Tyr His Arg
        130

<210> SEQ ID NO 8
<211> LENGTH: 132
<212> TYPE: PRT
<213> ORGANISM: Beet necrotic yellow vein virus
```

```
<400> SEQUENCE: 8

Met Val Leu Val Val Lys Val Asp Leu Ser Asn Ile Val Leu Tyr Ile
1               5                   10                  15

Val Ala Gly Cys Val Val Ser Met Leu Tyr Ser Pro Phe Phe Ser
            20                  25                  30

Asn Asp Val Lys Ala Ser Ser Tyr Ala Gly Ala Ile Phe Lys Gly Ser
        35                  40                  45

Gly Cys Ile Met Asp Arg Asn Ser Phe Ala Gln Phe Gly Ser Cys Asp
    50                  55                  60

Ile Pro Lys His Val Ala Glu Ser Ile Thr Lys Val Ala Thr Lys Glu
65                  70                  75                  80

His Asp Val Asp Ile Met Val Lys Arg Gly Glu Val Thr Val Arg Val
                85                  90                  95

Val Thr Leu Thr Glu Thr Ile Phe Ile Ile Leu Ser Arg Leu Phe Gly
            100                 105                 110

Leu Ala Val Phe Leu Phe Met Ile Cys Leu Met Ser Ile Val Trp Phe
            115                 120                 125

Trp Tyr His Arg
        130

<210> SEQ ID NO 9
<211> LENGTH: 902
<212> TYPE: DNA
<213> ORGANISM: Artificial Sequence
<220> FEATURE:
<223> OTHER INFORMATION: hp15 construct 2: with a 91 nt long beet intron
      sequence

<400> SEQUENCE: 9
atcgtgcttg tggttaaagt agatttatct aatattgtat tgtacatagt tgccggttgt      60
gttgttgtca gtatgttgta ctcaccgttt tcagcaacg atgttaaagc gtccagctat     120
gcgggagcaa ttttaaagg gagcggctgt atcatggccg cgaattcgtt tgctcaattt     180
gggagttgcg atattccaaa gcatgtagcc gagtccatca ctaaggttgc accaaagag     240 cacgatgttg acataatggt aaaaggggt gaagtgaccg ttcgtgttgt gactctcacc     300
gaaactattt ttataatatt atctagattg ttttggtttgg cggtgttttt gttcatgata     360
tgtttaatgt ctatagtttg gttttggtat catagacaag gtacctaaat cctggtttta     420
tatgtactac tgttgtagct gaaatttagg tcttcttgct gaaatttatt tctgtttcgt     480
tttcactgtt attcagtatc gatttgtcta tgataccaaa accaaactat agacattaaa     540
catatcatga acaaaaacac cgccaaacca acaatctag ataatattat aaaaatagtt     600
tcggtgagag tcacaacacg aacggtcact tcaccccttt ttaccattat gtcaacatcg     660
tgctctttgg tggcaacctt agtgatggac tcggctacat gctttggaat atcgcaactc     720
ccaaattgag caaacgaatt cgcggccatg atacagccgc tccctttaaa aattgctccc     780
gcatagctgg acgctttaac atcgttgctg aaaaacggtg agtacaacat actgacaaca     840
acacaaccgg caactatgta caatacaata ttagataaat ctactttaac cacaagcacg     900
at                                                                    902

<210> SEQ ID NO 10
<211> LENGTH: 399
<212> TYPE: DNA
<213> ORGANISM: Artificial Sequence
<220> FEATURE:
<223> OTHER INFORMATION: Sense p15 sequence (based on a modified
```

BNP15-Ala4 sequence)

<400> SEQUENCE: 10

| atcgtgcttg tggttaaagt agatttatct aatattgtat tgtacatagt tgccggttgt | 60 |
| gttgttgtca gtatgttgta ctcaccgttt ttcagcaacg atgttaaagc gtccagctat | 120 |
| gcgggagcaa ttttttaaagg gagcggctgt atcatggccg cgaattcgtt tgctcaattt | 180 |
| gggagttgcg atattccaaa gcatgtagcc gagtccatca ctaaggttgc caccaaagag | 240 |
| cacgatgttg acataatggt aaaaggggt gaagtgaccg ttcgtgttgt gactctcacc | 300 |
| gaaactattt ttataatatt atctagattg tttggtttgg cggtgttttt gttcatgata | 360 |
| tgtttaatgt ctatagtttg gttttggtat catagacaa | 399 |

<210> SEQ ID NO 11
<211> LENGTH: 91
<212> TYPE: DNA
<213> ORGANISM: Artificial Sequence
<220> FEATURE:
<223> OTHER INFORMATION: Intron sequence (derived from beet): 91 nt long

<400> SEQUENCE: 11

| tcctggtttt atatgtacta ctgttgtagc tgaaatttag gtcttcttgc tgaaatttat | 60 |
| ttctgtttcg ttttcactgt tattcagtat c | 91 |

<210> SEQ ID NO 12
<211> LENGTH: 399
<212> TYPE: DNA
<213> ORGANISM: Artificial Sequence
<220> FEATURE:
<223> OTHER INFORMATION: Antisense p15 sequence (based on a BNP15-Ala4 sequence)

<400> SEQUENCE: 12

| ttgtctatga taccaaaacc aaactataga cattaaacat atcatgaaca aaaacaccgc | 60 |
| caaaccaaac aatctagata atattataaa aatagtttcg gtgagagtca caacacgaac | 120 |
| ggtcacttca ccccttttta ccattatgtc aacatcgtgc tctttggtgg caaccttagt | 180 |
| gatggactcg gctacatgct tggaatatc gcaactccca aattgagcaa acgaattcgc | 240 |
| ggccatgata cagccgctcc ctttaaaaat tgctcccgca tagctggacg ctttaacatc | 300 |
| gttgctgaaa acggtgagt acaacatact gacaacaaca caaccggcaa ctatgtacaa | 360 |
| tacaatatta gataaatcta ctttaaccac aagcacgat | 399 |

<210> SEQ ID NO 13
<211> LENGTH: 1360
<212> TYPE: DNA
<213> ORGANISM: Artificial Sequence
<220> FEATURE:
<223> OTHER INFORMATION: hp15 construct 3: with a 555 nt long beet intron sequence

<400> SEQUENCE: 13

| atcgtgcttg tggttaaagt agatttatct aatattgtat tgtacatagt tgccggttgt | 60 |
| gttgttgtca gtatgttgta ctcaccgttt ttcagcaacg atgttaaagc gtccagctat | 120 |
| gcgggagcaa ttttttaaagg gagcggctgt atcatggccg cgaattcgtt tgctcaattt | 180 |
| gggagttgcg atattccaaa gcatgtagcc gagtccatca ctaaggttgc caccaaagag | 240 |
| cacgatgttg acataatggt aaaaggggt gaagtgaccg ttcgtgttgt gactctcacc | 300 |
| gaaactattt ttataatatt atctagattg tttggtttgg cggtgttttt gttcatgata | 360 |

-continued

```
tgtttaatgt ctatagtttg gttttggtat catagacaag gtaccacgtt tttctctctc    420 ctaattttc tcactttttt ttcatctcat tctgttttat gttctgtgaa tttattagta     480
gatttatcta cttttctatc taattttgac gctagattaa tgattcagtt ttattattac    540
attttccgga aaattggtta agtttgata atttaaatga ttttttttcc gtgatcaaat     600
tgtagaaatt gtttaagttc gatagtttat atctttatga attttttgtgt ttgatctgat   660 gatagtttta gtgattattg taactttga aagtgtgtgt ttttatgtgt gtagcgattt     720
gtatagtaaa taagattaat gatcatggct aaattatggc gtaggttaat tttagaagaa    780 agtattttt tgctaaattg aagtcatctg cgtcgtatta ttgcgatttc tgcactttta     840
ctagctgaat tgagtttgct gattggatat tctttatgat tgaagttgtt ttgctattga    900
atattcttta tgagattttt gaatgaagat ttttctgtaa ttaatgat caggtatcga      960 tttgtctatg ataccaaaac caaactatag acattaaaca tatcatgaac aaaaacaccg    1020
ccaaaccaaa caatctagat aatattataa aaatagtttc ggtgagagtc acaacacgaa    1080
cggtcacttc accccttttt accattatgt caacatcgtg ctctttggtg gcaaccttag    1140
tgatggactc ggctacatgc tttggaatat cgcaactccc aaattgagca aacgaattcg    1200
cggccatgat acagccgctc cctttaaaaa ttgctcccgc atagctggac gctttaacat    1260
cgttgctgaa aaacggtgag tacaacatac tgacaacaac acaaccggca actatgtaca    1320
atacaatatt agataaatct actttaacca caagcacgat                          1360
```

<210> SEQ ID NO 14
<211> LENGTH: 550
<212> TYPE: DNA
<213> ORGANISM: Artificial Sequence
<220> FEATURE:
<223> OTHER INFORMATION: Intron sequence (derived from beet): 550 nt long

<400> SEQUENCE: 14

```
acgtttttct ctctcctaat ttttctcact ttttttcat ctcattctgt tttatgttct     60
gtgaatttat tagtagattt atctactttt ctatctaatt ttgacgctag attaatgatt    120
cagttttatt attacatttt ccggaaaatt ggttaagttt tgataattta aatgattttt    180
tttccgtgat caaattgtag aaattgttta agttcgatag tttatatctt tatgaatttt    240
tgtgtttgat ctgatgatag ttttagtgat tattgtaact tttgaaagtg tgtgttttta    300
tgtgtgtagc gatttgtata gtaaataaga ttaatgatca tggctaaatt atggcgtagg    360 ttaatttag aagaaagtat tttttgcta aattgaagtc atctgcgtcg tattattgcg       420
atttctgcac tttttactagc tgaattgagt ttgctgattg gatattcttt atgattgaag   480 ttgtttgct attgaatatt ctttatgaga ttttgaatg aagatttttc tgtaattaat      540
atgatcaggt                                                            550
```